United States Patent [19]

Isakson et al.

[11] Patent Number: 6,045,773
[45] Date of Patent: Apr. 4, 2000

[54] METHOD OF DETECTING CYCLOOXYGENASE-2

[75] Inventors: Peter C Isakson, Clarkson Valley; Karen Seibert; John J Talley, both of St. Louis, all of Mo.

[73] Assignee: G.D. Searle & Co., Skokie, Ill.

[21] Appl. No.: 09/256,739

[22] Filed: Feb. 24, 1999

Related U.S. Application Data

[63] Continuation of application No. 08/731,618, Oct. 16, 1996, abandoned.
[60] Provisional application No. 60/005,686, Oct. 17, 1995.

[51] Int. Cl.[7] .................................................... A61K 51/04
[52] U.S. Cl. ................. 424/1.81; 424/1.85; 424/1.89; 424/1.65; 424/1.37; 424/1.45; 424/1.41; 424/9.1; 424/9.6
[58] Field of Search ................... 424/1.81, 1.85, 424/1.65, 1.41, 1.45, 1.89, 1.37, 9.1, 9.6, 9.7; 514/406, 407, 403, 317, 326

[56] References Cited

U.S. PATENT DOCUMENTS

| | | | |
|---|---|---|---|
| 5,173,496 | 12/1992 | Bruneau et al. | 514/338 |
| 5,213,787 | 5/1993 | Wilbur et al. | 424/1.1 |
| 5,393,790 | 2/1995 | Reitz et al. | 514/709 |
| 5,459,239 | 10/1995 | O'Neill et al. | 530/327 |
| 5,474,995 | 12/1995 | Ducharme et al. | 514/241 |

FOREIGN PATENT DOCUMENTS

| | | |
|---|---|---|
| WO94/13635 | 6/1994 | WIPO |
| WO94/15932 | 7/1994 | WIPO |
| WO94/20480 | 9/1994 | WIPO |
| WO94/26731 | 11/1994 | WIPO |
| WO94/27980 | 12/1994 | WIPO |
| WO95/00501 | 1/1995 | WIPO |
| WO95/05395 | 2/1995 | WIPO |
| WO95/11883 | 5/1995 | WIPO |
| WO95/15316 | 6/1995 | WIPO |
| WO96/03387 | 2/1996 | WIPO |
| WO96/03388 | 2/1996 | WIPO |

OTHER PUBLICATIONS

Bertenshaw, Biomed. And Med. Chem. Lett., 5:2919–22:1995.
Huang et al, J. Med. Chem., 39:253–66:1996.
Li et al, J. Med. Chem., 38:4570–78:1995.
Li et al, J. Med. Chem., 39:1846–56:1996.
McCarthy et al, J. Chem. Ed., 71:830–36:1994.
Br. Heart J., 57:23:1987, Bell et al.
Acta Radio Supp., 376:148:1991, Jones et al.
Opthalmic Res., 18:292:1986, Kiyosawa et al.
Todd, Dissertation Abstracts. Int., 52:2566–B:1991.
McCarthy et al, J. of Nuc. Med., 36:49:1995.
Patrono et al, Chem. Abstracts, 95:214725:1981.
De Rosario et al, J. of Nuc. Med., 37:192:1996.
Hla et al, Proc. Natl. Acad. Sci USA, 89:7384:1992.
Masferrer et al, Proc. Natl. Acad. Sci. USA, 89:3917:1992.
Sano et al, Cancer Res., 55:3785–9:1995.
Patrono,AAS 7, pp. 256–259 (1980).

*Primary Examiner*—Jose' G. Dees
*Assistant Examiner*—Michael G. Hartley
*Attorney, Agent, or Firm*—Joseph W. Bulock

[57] ABSTRACT

The invention relates to a method of detecting concentrations of cyclooxygenase-2 in a mammal, the method comprising: administering to the mammal a diagnostically effective amount of a cyclooxygenase-2 selective agent, which is capable of being detected in vivo; and b) detecting the agent so the concentration of cyclooxygenase-2 is detected.

23 Claims, No Drawings

METHOD OF DETECTING CYCLOOXYGENASE-2

This is a continuation of application Ser. No. 08/731,618 filed Oct. 16, 1996 now abandoned, which application claims priority of Provisional application Ser. No. 60/005,686, filed Oct. 17, 1995.

BACKGROUND OF THE INVENTION

Prostaglandins play a major role in the inflammation process. The inhibition of prostaglandin production, especially production of $PGG_2$, $PGH_2$ and $PGE_2$, has been a common target of antiinflammatory drug discovery. Non-steroidal antiinflammatory drugs (NSAID's) have been found to prevent the production of prostaglandin-induced pain and swelling associated with the inflammation process by inhibiting enzymes in the human arachidonic acid/prostaglandin pathway, including the enzyme cyclooxygenase (now identified as COX-1). Recently, the sequence of another heretofore unknown enzyme in the human arachidonic acid/prostaglandin pathway has been reported by T. Hla and K. Nielson, *Proc. Natl. Acad. Sci, USA*, 89, 7384 (1992) and named "cyclooxygenase-2 (COX-2)" or "prostaglandin G/H synthase II". The expression of COX-2 is readily induced in response to pro-inflammatory stimuli in cells in vivo, including macrophages, monocytes, synovial cells and endothelial cells. Cyclooxygenase-2 is inducible by cytokines or endotoxins and such induction is inhibited by glucocortoids (J. Masferrer et al., *Proc. Natl. Acad. Sci, USA*, 89, 3917 (1992)).

The biological importance and distribution of cyclooxygenase isoforms is becoming known. It has been observed that COX-2 is induced in parallel with the development of inflammation and prostaglandin production in common inflammation and arthritis models. COX-2 expression also has been observed in cancer cells, such as colorectal cancer (H. Sano et al, *Cancer Res.*, 55, 3785–9 (1995)).

Various compounds have been described as COX-2 inhibitors. S. Bertenshaw describes thiophene compounds which selectively inhibit COX-2 [*Biomed. and Med. Chem. Lett.*, 5, 2919–22 (1995)]. H. Huang et al. [*J. Med. Chem.*, 39, 253–66 (1996)] describe diarylspiro[2.4]heptenes as highly selective COX-2 inhibitors. J. Li et al. [*J. Med. Chem.*, 38, 4570–78 (1995)] describe diarylcyclopentenes as highly selective COX-2 inhibitors. J. Li et al. [*J. Med. Chem.*, 39, 1846–56 (1996)] describe terphenyl compounds as highly selective COX-2 inhibitors.

Compounds which selectively inhibit cyclooxygenase-2 have been described in U.S. Pat. Nos. 5,393,790, 5,474,995 and WO documents WO94/15932, WO94/27980, WO95/00501, WO94/13635, WO94/20480, WO95/11883, WO95/05395, WO95/15316, WO96/03388, WO96/03387 and WO94/26731.

The use of nuclear medicine and nuclear magnetic resonance, including X-ray, NMR and MRI, has been described for analyzing tissue, especially bone and soft tissue, such as cartilage, synovium and organs.

Positron-emission tomography (PET) also has been used for visualizing a patient's condition. In PET, compounds labeled with positron-emitting radioisotopes are administered to a patient and detected so as to quantify the distribution of radioactivity. Common radioisotopes found useful in PET include $^{11}C$, $^{15}O$, $^{13}N$, $^{18}F$, $^{62}Cu$ and $^{64}Cu$, especially where incorporated in perfusion agents, metabolism agents, receptor-based radiopharmaceuticals and receptor-based systems [T. McCarthy et al., *J. Chem. Ed.*, 71, 830–36 (1994)].

Various methods have been used to image inflammatory responses and conditions. Indium-111 labeled neutrophils have been described in imaging the inflammatory response to myocardial infarctions [*Br. Heart J.*, 57, 23 (1987)].

2-Deoxy-2-($^{18}F$)fluoro-D-glucose (FDG) is one of the more established metabolism agents for detecting inflammation by positron tomography. It has been used to measure pulmonary inflammation [*Acta. Radio. Supp.*, 376, 148 (1991). It has also been described for use in diagnosing the presence of tumors [*Ophthalmic. Res.*, 18, 292 (1986)].

The synthesis and in vivo distribution of $^{18}F$-flurbiprofen was described by Stewart Todd [*Dissertation Abstracts. Int.*, 52, 2566-B (1991)]. However, fluribiorofen is non-selective as it inhibits both COX-1 and COX-2, and PET analysis would present a high background during in vivo analysis due to COX-1 detection.

Although the use of radiation emitting pharmaceuticals has proven useful in non-invasive imaging, there still exists a need for more selective non-invasive diagnostic techniques to identify early detection of disease, such as arthritis, CNS-disorders and injuries, and neoplasia, as well as monitoring effectiveness of treatment.

DETAILED DESCRIPTION OF THE INVENTION

This invention relates to a method of detecting cyclooxygenase-2. Specifically, the invention relates to a method of detecting a concentration of cyclooxygenase-2 in a mammal, the method comprising: administering to the mammal a diagnostically effective amount of a cyclooxygenase-2 selective agent, which is capable of being detected in vivo; and b) detecting the agent so the concentration of cyclooxygenase-2 is detected.

The invention also includes a method of localizing and quantifying cyclooxygenase-2 in a mammal, said method comprising a) preparing a labeled compound, which selectively binds to cyclooxygenase-2 and which contains an isotope capable of emitting radiation; b) administering to said mammal a diagnostically effective amount of the labeled compound; and c) detecting an emission from the compound administered to the mammal so that the cyclooxygenase-2 in the mammal is localized.

The invention also includes a method of detecting neoplasia in a mammal, said method comprising a) preparing a compound which selectively binds to cyclooxygenase-2 and which is labeled with an isotope capable of emitting gamma or positron radiation b) administering to said mammal a diagnostically effective amount of the labeled compound; and c) detecting an emission from the compound administered to the mammal so that the neoplasia in the mammal is localized.

Preferably, the agent is prepared by labeling a cyclooxygenase-2 selective compound with an isotope capable of being detected in vivo.

More preferably the compound which selectively inhibits cyclooxygenase-2 is selected from compounds of Formula I

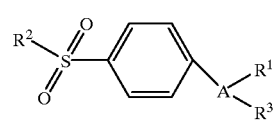

I wherein A is a 5- or 6-member ring substituent
wherein A is a ring substituent selected from partially unsaturated heterocyclyl, heteroaryl, cycloalkenyl and aryl;

wherein $R^1$ is at least one substituent selected from heteroaryl, cycloalkyl, cycloalkenyl and aryl, wherein $R^1$ is substituted with one or more radicals convertible to a detectable isotope;

wherein $R^2$ is methyl or amino; and wherein $R^3$ is one or more radical-s selected from hydrido, halo, alkyl, alkenyl, alkynyl, oxo, cyano, carboxyl, cyanoalkyl, heterocyclooxy, alkyloxy, alkylthio, alkylcarbonyl, cycloalkyl, aryl, haloalkyl, heterocyclo, cycloalkenyl, aralkyl, heterocycloalkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkylthioalkyl, aralkoxyalkyl, alkoxyaralkoxyalkyl, alkoxycarbonylalkyl, aminocarbonyl, aminocarbonylalkyl, alkylaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, N-alkyl-N-arylaminosulonyl; or a pharmaceutically-acceptable salt or a prodrug thereof.

A more preferred class of compounds which inhibit cyclooxygenase-2 consists of compounds of Formula I wherein A is a radical selected from thienyl, oxazolyl, furyl, pyrrolyl, thiazolyl, imidazolyl, benzofuryl, indenyl, benzothienyl, isoxazolyl, pyrazolyl, cyclopentenyl, cyclopentadienyl, benzindazolyl, benzopyranopyrazolyl, phenyl, and pyridyl; wherein $R^1$ is selected from 5- and 6-membered heteroaryl, and aryl selected from phenyl, biphenyl and naphthyl, wherein $R^1$ is substituted at a substitutable position with one or more radicals selected from hydroxy, alkoxy, nitro, triflate, halo, and formyl; wherein $R^2$ is methyl or amino; and wherein $R^3$ is a radical selected from hydrido, oxo, cyano, carboxyl, lower alkoxycarbonyl, lower carboxyalkyl, lower cyanoalkyl, halo, lower alkyl, lower alkyloxy, lower cycloalkyl, phenyl, lower haloalkyl, 5- or 6-membered heterocyclo, lower hydroxylalkyl, lower aralkyl, acyl, phenylcarbonyl, lower alkoxyalkyl, 5- or 6-membered heteroaryloxy, aminocarbonyl, lower alkylaminocarbonyl, lower alkylamino, lower aminoalkyl, lower alkylaminoalkyl, phenyloxy, and lower aralkoxy; or a pharmaceutically-acceptable salt or a prodrug thereof.

An even more preferred class of compounds which inhibit cyclooxygenase-2 consists of compounds of Formula I wherein A is selected from furyl, oxazolyl, isoxazolyl, imidazolyl, and pyrazolyl; wherein $R^1$ is phenyl substituted at a substitutable position with one or more radicals selected from hydroxy, nitro, triflate, halo, and formyl; wherein $R^2$ is methyl or amino; and wherein $R^3$ is a radical selected from hydrido, oxo, cyano, carboxyl, methoxycarbonyl, ethoxycarbonyl, carboxypropyl, carboxymethyl, carboxyethyl, cyanomethyl, fluoro, chloro, bromo, methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, methoxy, ethoxy, propoxy, n-butoxy, pentoxy, cyclohexyl, phenyl, pyridyl, thienyl, thiazolyl, oxazolyl, furyl, pyrazinyl, hydroxylmethyl, hydroxylpropyl, benzyl, formyl, phenylcarbonyl, methoxymethyl, furylmethyloxy, aminocarbonyl, N-methylaminocarbonyl, N,N-dimethylaminocarbonyl, N,N-dimethylamino, N-ethylamino, N,N-dipropylamino, N-butylamino, N-methyl-N-ethylamino, aminomethyl, N,N-dimethylaminomethyl, N-methyl-N-ethylaminomethyl, benzyloxy, and phenyloxy; or a pharmaceutically-acceptable salt or prodrug thereof.

A family of specific compounds of particular interest within Formula I consists of compounds and pharmaceutically-acceptable salts and prodrugs thereof as follows:

4-[3-(hydroxymethyl)-5-(4-nitrophenyl)-1H-pyrazol-1-yl]benzenesulfonamide;

4-[3-(difluoromethyl)-5-(4-hydroxyphenyl)-1H-pyrazol-1-yl]benzenesulfonamide;

4-[5-(4-hydroxyphenyl)-3-trifluoromethyl-1H-pyrazol-1-yl]benzenesulfonamide;

4-[3-(hydroxymethyl)-5-(4-hydroxyphenyl)-1H-pyrazol-1-yl]benzenesulfonamide;

4-hydroxy-5-[1-[4-(methylsulfonyl)phenyl]-4-trifluoromethyl-1H-imidazol-2-yl]pyridine;

4-[2-(4-hydroxypyridin-3-yl) -4-(trifluoromethyl)-1H-imidazol-1-yl]benzenesulfonamide;

4-[5-methyl-3-(4-hydroxyphenyl)isoxazol-4-yl] benzenesulfonamide;

4-[5-hydroxymethyl-3-(4-hydroxyphenyl) isoxazol-4-yl] benzenesulfonamide;

4-[2-methyl-4-(4-hydroxyphenyl)-5-oxazolyl] benzenesulfonamide;

4-[5-(4-hydroxyphenyl)-2-(trifluoromethyl)-4-oxazolyl] benzenesulfonamide;

4-[3-(difluoromethyl)-5-(3-iodo-4-hydroxyphenyl)-1H-pyrazol-1-yl]benzenesulfonamide;

4-[5-(3-iodo-4-hydroxyphenyl)-3-trifluoromethyl-1H-pyrazol-1-yl]benzenesulfonamide;

4-[3-(hydroxymethyl)-5-(3-iodo-4-hydroxyphenyl)-1H-pyrazol-1-yl]benzenesulfonamide;

4-[3-(difluoromethyl)-5-(4-nitrophenyl)-1H-pyrazol-1-yl]benzenesulfonamide;

4-[5-(4-nitrophenyl)-3-(trifluoromethyl)-1H-pyrazol-1-yl]benzenesulfonamide;

4-[3-(difluoromethyl)-5-(4-nitrophenyl)-1H-pyrazol-1-yl]benzenesulfonamide;

4-nitro-5-[1-[4-(methylsulfonyl)phenyl]-4-trifluoromethyl-1H-imidazol-2-yl]pyridine;

4-[2-(4-nitropyridin-3-yl)-4-(trifluoromethyl)-1H-imidazol-1-yl]benzenesulfonamide;

4-[5-methyl-3-(4-nitrophenyl)isoxazol-4-yl] benzenesulfonamide;

4-[5-hydroxymethyl-3-(4-nitrophenyl)isoxazol-4-yl] benzenesulfonamide;

4-[2-methyl-4-(4-nitrophenyl)-5-oxazolyl] benzenesulfonamide; and

4-[5-(4-nitrophenyl)-2-(trifluoromethyl)-4-oxazolyl] benzenesulfonamide.

There are many different labels and methods of labeling known to those of ordinary skill in the art. Examples of the types of labels which can be used in the present invention include radioactive isotopes and paramagnetic isotopes. Those of ordinary skill in the art will know of other suitable labels for binding to the compounds used in the invention, or will be able to ascertain such, using routine experimentation. Furthermore, the binding of these labels to the compounds can be done using standard techniques common to those of ordinary skill in the art. For diagnostic in vivo imaging, the type of detection instrument available is a major factor in selecting a given radionuclide. The radionuclide chosen must have a type of decay which is detectable for a given type of instrument. In general, any conventional method for visualizing diagnostic imaging can be utilized in accordance with this invention. Another important factor in selecting a radionuclide for in vivo diagnosis is that the half-life of a radionuclide be long enough so that it is still detectable at the time of maximum uptake by the target, but short enough so that deleterious radiation upon the host is minimized. Ideally, a radionuclide used for in vivo imaging will lack a particulate emission, but produce a large number of photons in a 140–200 keV range, which may be readily detected by conventional gamma cameras.

Preferably, the isotope is capable of being detected by PET. Typical positron emitting nuclides like carbon-11, selenium-73 and fluorine-18 enable the in vivo application of the labeled compounds by the PET technique. By using this technique, a computer tomogram can be obtained of the tissue or organ to be investigated, e.g. the colon, joints or the brain, enabling the localization and quantification of cyclooxygenase-2. In the PAT technique, very short living radioisotopes are used which emit positrons, for example carbon-11 and fluorine-18 with half-lives of 20 and 110 minutes respectively.

Gamma radiation emitting isotopes like bromine-76, bromine-77, iodine-125 and iodine-123 can be used for the labeling of compounds to be detected by conventional scanning techniques or in the so-called "single photon emission computer tomography" (SPECT) technique. By using conventional scanning techniques, the emitted gamma radiation can be detected by suitable apparatuses, e.g. a gamma camera, to produce images of the tissue or organ to be investigated. The more advanced SPECT technique is also based upon the detection of gamma radiation by sensible detectors.

More preferably, the compound is labeled with one or more isotopes selected from fluorine-18 ($^{18}F$), carbon-11 ($^{11}C$), bromine-76 ($^{76}Br$), bromine-77 ($^{77}Br$), and iodine-123 ($^{123}I$). Even more preferably, the compound is labeled with $^{11}C$ or $^{13}F$.

A family of specific labeled agents of particular interest consists of compounds and pharmaceutically-acceptable salts thereof as follows:

4-[3-(hydroxymethyl)-5-[4-($^{18}F$) fluorophenyl]-1H-pyrazol-1-yl]benzenesulfonamide;
4-[3-(difluoromethyl)-5-[4-($^{11}C$)methoxyphenyl]-1H-pyrazol-1-yl]benzenesulfonamide;
4-[5-[4-($^{11}C$)methoxyphenyl]-3-trifluoromethyl-1H-pyrazol-1-yl]benzenesulfonamide;
4-[3-(hydroxymethyl)-5-[4-($^{11}C$)methoxyphenyl]-1H-pyrazol-1-yl]benzenesulfonamide;
4-($^{11}C$)methoxy-5-[1-[4-(methylsulfonyl)phenyl]-4-trifluoromethyl-1H-imidazol-2-yl]pyridine;
4-[2-(4-($^{11}C$)methoxypyridin-3-yl)-4-(trifluoromethyl)-1H-imidazol-1-yl]benzenesulfonamide;
4-[5-methyl-3-[4-($^{11}C$)methoxyphenyl]isoxazol-4-yl]benzenesulfonamide;
4-[5-hydroxymethyl-3-[4-($^{11}C$)methoxyphenyl]isoxazol-4-yl]benzenesulfonamide;
4-[2-methyl-4-[4-($^{11}C$)methoxyphenyl]-5-oxazolyl]benzenesulfonamide; and
4-[5-[4-($^{11}C$)methoxyphenyl]-2-(trifluoromethyl)-4-oxazolyl]benzenesulfonamide.
4-[3-(difluoromethyl)-5-[3-($^{125}I$)iodo-4-($^{11}C$)methoxyphenyl]-1H-pyrazol-1-yl]benzenesulfonamide;
4-[5-[3-($^{125}I$) iodo-4-($^{11}C$)methoxyphenyl]-3-trifluoromethyl-1H-pyrazol-1-yl]benzenesulfonamide;
4-[5-(4-hydroxy-3-($^{125}I$) iodophenyl)-3-trifluoromethyl-1H-pyrazol-1-yl]benzenesulfonamide;
4-[3-(hydroxymethyl)-5-[3-($^{125}I$)iodo-4-($^{11}C$)methoxyphenyl]-1H-pyrazol-1-yl]benzenesulfonamide;

4-[3-(difluoromethyl)-5-4-($^{18}F$) fluorophenyl]-1H-pyrazol-1-yl]benzenesulfonamide;
4-[5-[4-($^{18}F$)fluorophenyl]-3-(trifluoromethyl)-1H-pyrazol-1-yl]benzenesulfonamide;
4-[3-(difluoromethyl)-5-[4-($^{18}F$) fluorophenyl]-1H-pyrazol-1-yl]benzenesulfonamide;
4-($^{18}F$)fluoro-5-[1-[4-(methylsulfonyl)phenyl]-4-trifluoromethyl-1H-imidazol-2-yl]pyridine;
4-[2-[4-($^{18}F$)fluoropyridin-3-yl]-4-(trifluoromethyl))-1H-imidazol-1-yl]benzenesulfonamide;
4-[5-methyl-3-[4-($^{18}F$)fluorophenyl]isoxazol-4-yl]benzenesulfonamide;
4-[5-hydroxymethyl-3-[4-($^{18}F$) fluorophenyl]isoxazol-4-yl]benzenesulfonamide;
4-[2-methyl-4-[4-($^{18}F$) fluorophenyl]-5-oxazolyl]benzenesulfonamide; and
4-[5-[4-($^{18}F$)fluorophenyl]-2-(trifluoromethyl)-4-oxazolyl]benzenesulfonamide The compounds used in the method of the invention can also be labeled with paramagnetic isotopes for purposes of in vivo diagnosis.

The invention also includes a method of localizing and quantifying cyclooxygenase-2 in a the method comprising: preparing a compound which selectively binds to cyclooxygenase-2 and which is labeled with an isotope capable of emitting gamma radiation; administering to said mammal a diagnostically effective amount of the labeled compound; and c) detecting the gamma emission from the compound administered to the mammal so that the cyclooxygenase-2 in the mammal is localized.

The invention can be used to measure cyclooxygenase-2 in humans and other metals in various medicinal and veterinary applications. The invention can be used to measure cyclooxygenase-2 in cyclooxygenase-2 associated diseases, conditions and disorders including arthritis, including but not limited to rheumatoid arthritis, spondyloarthropathies, gouty arthritis, osteoarthritis, systemic lupus erythematosus and juvenile arthritis, auto-immune disease, allograft rejection, asthma, bronchitis, tendinitis, bursitis, and skin related conditions such as psoriasis, eczema, burns and dermatitis, post-operative inflammation including from ophthalmic surgery such as cataract surgery and refractive surgery, gastrointestinal conditions such as inflammatory bowel disease, Crohn's disease, gastritis, irritable bowel syndrome and ulcerative colitis, neoplasia, such as colorectal cancer, and cancer of the breast, lung, prostate, bladder, cervix and skin, vascular diseases, migraine headaches, periarterits nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, neohritiis, hypersensitivity, conjunctivitis, swelling occurring after injury, myocardial ischemia, myochardial infarction, ophthalmic diseases, such as retinitis, retinopathies, uveitis, ocular photophobia, and of acute injury to the eye tissue, allergic rhinitis, respiratory distress syndrome, endotoxin shock syndrome, atherosclerosis, pulmonary inflammation such as from viral and bacterial infections and from cystic fibrosis, central nervous system disorders, such as cortical dementias including Alzheimer's disease, and central nervous system damage resulting from stroke, ischemia and trauma.

More preferably, the detected cyclooxygenase-2 is associated with a condition selected from inflammation, arthritis, neoplasia and central nervous system disorders.

Alternatively, the method of the invention can be used to monitor the course of inflammation in an individual. Thus, by measuring the increase or decrease in the size or number of inflammatory sites it would be possible to determine whether a particular therapeutic regimen aimed at ameliorating the cause of the inflammatory process, or the inflammatory process itself, is effective.

Another embodiment of the invention includes a method for diagnosing the specific underlying cause of a cyclooxygenase-2 associated disorder at the site. In this method an individual suspected of having a cyclooxygenase-2 associated disorder is first administered a diagnostically effective amount of agent, as previously described. The individual suspected of having a cyclooxygenase-2 associated disorder site cyclooxygenase-2 associated disorder. After determining the specific cause of the site it is then possible to administer a therapeutic agent For the underlying cause of the process at the site or to surgically remove the site.

The invention further relates to a pharmaceutical composition to be used for the method defined, comprising in addition to a pharmaceutically acceptable carrier and, if desired, at least one pharmaceutical acceptable adjuvant, as the active substance a radiolabeled cyclooxygenase-2 selective agent or radiolabeled prodrug thereof, in a diagnostically effective quantity. If desired, said composition may be brought into a form more suitable for intravenous or subcutaneous administration, for example by the addition of a pharmaceutically acceptable liquid vehicle, preferably a physiological saline solution. The composition should be sterile for intravenous or subcutaneous administration. If desired, one or more adjuvants may be present in the composition, for example suitable stabilizers like ascorbic acid, gentisic acid or salts of these acids, and/or fillers like glucose, lactose mannitol etc. Dependent on the investigation to be performed and the results desired by performing these experiments, the composition may be administered to the living being, preferably a human being, at once, as a bolus injection, or gradually by a continuous infusion.

The pharmaceutical composition is administered in a dose of 0.01 mCi to 10 mCi and preferably about 2–5 mCi. The administration dose per subject is usually in the range of about 10–30 mCi.

The invention also includes a method of preparing cyclooxygenase-2 inhibitors containing a label which allows in vivo detection by PET. Preferably, the label is incorporated by halide exchange of a nitro radical or by alkylation of alcohols.

A "cyclooxygenase-2 selective agent" is a compound which selectively interacts with the cyclooxygenase-2 enzyme and contains a label which is detectable by imaging means. Preferably, the labeled compound has high specific activity. More preferably, the agent will have a specific activity of more than about 1000 Ci/mmol. Preferably, the agent will have a clearance half-time of less than about 60 minutes. The concentration of observed agent in tissue should be proportional to the amount of COX-2 in the tissue.

The phrase "diagnostically effective" is intended to qualify the amount of each agent which will be detectable, while avoiding adverse side effects found with higher doses.

The quantity of radioactive material effective for diagnosing depends on various factors such as the diagnostic method, e.g. planar scintigraphy or emission tomography, the radiolabel used and the tissue or organ to be examined. The quantity of radioactive material which is effective for diagnosing purposes may vary within broad ranges. Generally the radioactive material is administered to the living being in a quantity of 1 to 1000 MBq per 70 kg of body weight. The radiolabel may be chosen from radionuclides selected from the group consisting of positron emitting nuclides and gamla radiation emitting nuclides.

The term "hydrido" denotes a single hydrogen atom (H). This hydrido radical may be attached, for example, to an oxygen atom to form a hydroxyl radical or two hydrido radicals may be attached to a carbon atom to form a methylene ($—CH_2—$) radical. There used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals having at least one carbon-carbon double bond of two to about twenty carbon atoms or, preferably, one to about twelve carbon atoms. More preferred alkyl radicals are "lower alkenyl" radicals having two to about six carbon atoms. Examples of alkenyl radicals include ethenyl, propenyl, allyl, propenyl, butenyl and 4-methylbutenyl. The term "alkynyl" denotes linear or branched radicals having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about six carbon atoms. Examples of such radicals include propargyl, butynyl, and the like. The terms "alkenyl", "lower alkenyl", embrace radicals having "cis" and "trans" orientations, or alternatively, "E" and "Z" orientations. The term "cycloalkyl" embraces saturated carbocyclic radicals having three to twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "cycloalkenyl" embraces partially unsaturated carbocyclic radicals having three to twelve carbon atoms. More preferred cycloalkenyl radicals are "lower cycloalkenyl" radicals having four to about eight carbon atoms. Examples of such radicals include cyclobutenyl, cyclopentenyl and cyclohexenyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkyloxy"

embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide haloalkoxy radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoromethoxy, fluoroethoxy and fluoropropoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Aryl moieties may also be substituted at a substitutable position with one or more substituents selected independently from alkyl, alkoxyalkyl, alkylaminoalkyl, carboxyalkyl, alkoxycarbonylalkyl, aminocarbonylalkyl, alkoxy, aralkoxy, hydroxyl, amino, halo, nitro, alkylamino, acyl, cyano, carboxy, aminocarbonyl, alkoxycarbonyl and aralkoxycarbonyl. The term "heterocyclo" embraces saturated, partially unsaturated and unsaturated heteroatom-containing ring-shaped radicals, where the heteroatoms may be selected from nitrogen, sulfur and oxygen. Examples of saturated heterocyclo radicals include saturated 3 to 6-membered heteromonocylic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclo radicals include dihydrothiophene, dihydropyran, dihydrofuran and dihydrothiazole. The term "heteroaryl" embraces unsaturated heterocyclo radicals. Examples of unsaturated heterocyclo radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclo group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b] pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclo group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclo group containing 1 to 2 sulfur atoms and 1 to 3 nitrogen atoms (e.g., benzothiazolyl, benzothiadiazolyl, etc.) and the like. The term also embraces radicals where heterocyclo radicals are fused with aryl radicals. Examples of such fused bicyclic radicals include benzofuran, benzothiophene, and the like. Said "heterocyclo group" may have 1 to 3 substituents such as alkyl, hydroxyl, halo, alkoxy, oxo, amino and alkylamino. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include methylthiomethyl. The term "alkylsulfinyl" embraces radicals containing a linear or branched alkyl radical, of one to ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as alkylsulfonyl, denotes respectively divalent radicals —$SO_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulonyl and propylsulfonyl. The "alkylsulfonyl" radicals may be further substituted with one or more halo atoms, such as fluoro, chloro or bromo, to provide haloalkylsulfonyl radicals. The terms "sulfamyl", "aminosulfonyl" and "sulfonamidyl" denote $NH_2O_2S$—. The term "acyl" denotes a radical provided by the residue after removal of hydroxyl from an organic acid. Examples of such acyl radicals include alkanoyl and aroyl radicals. Examples of such lower alkanoyl radicals include formyl, acetyl, propionyl, butyryl, isobutyryl, valeryl, isovaleryl, pivaloyl, hexanoyl, trifluoroacetyl. The term "carbonyl", whether used alone or with other terms, such as "alkoxycarbonyl", denotes —(C=O)—. The term "aroyl" embraces aryl radicals with a carbonyl radical as defined above. Examples of aroyl include benzoyl, naphthoyl, and the like and the aryl in said aroyl may be additionally substituted. The terms "carboxy" or "carboxyl", whether used alone or with other terms, such as "carboxyalkyl", denotes —$CO_2H$. The term "carboxyalkyl" embraces alkyl radicals substituted with a carboxy radical. More preferred are "lower carboxyalkyl" which embrace lower alkyl radicals as defined above, and may be additionally substituted on the alkyl radical with halo. Examples of such lower carboxyalkyl radicals include carboxymethyl, carboxyethyl and carboxypropyl. The term "alkoxycarbonyl" means a radical containing an alkoxy radical, as defined above, attached via an oxygen atom to a carbonyl radical. More preferred are "lower alkoxycarbonyl" radicals with alkyl portions having 1 to 6 carbons. Examples of such lower alkoxycarbonyl (ester) radicals include substituted or unsubstituted methoxycarbonyl, ethoxycarbonyl, propoxycarbonyl, butoxycarbonyl and hexyloxycarbonyl. The terms "alkylcarbonyl", "arylcarbonyl" and "aralkylcarbonyl" include radicals having alkyl, aryl and aralkyl radicals, as defined above, attached via an oxygen atom to a carbonyl radical. Examples of such radicals include substituted or unsubstituted methylcarbonyl, ethylcarbonyl, phenylcarbonyl and benzylcarbonyl. The term "aralkyl" embraces aryl-substituted alkyl radicals such as benzyl, diphenylmethyl, triphenylmethyl, phenylethyl, and diphenylethyl. The aryl in said aralkyl may be additionally substituted with halo, alkyl, alkoxy, halkoalkyl and haloalkoxy. The terms benzyl and phenylmethyl are interchangeable. The term "heterocycloalkyl" embraces saturated and partially unsaturated heterocyclo-substituted alkyl radicals, such as pyrrolidinylmethyl, and heteroaryl-substituted alkyl radicals, such as pyridylmethyl, quinolylmethyl, thienylmethyl, furylethyl, and quinolylethyl. The heteroaryl in said heteroaralkyl may be additionally substituted with halo, alkyl, alkoxy, halkoalkyl and haloalkoxy. The term "aralkoxy" embraces aralkyl radicals attached through an oxygen atom to other radicals. The term "aralkoxyalkyl" embraces aralkoxy radicals attached through an oxygen atom to an alkyl radical. The term "aralkylthio" embraces aralkyl radicals attached to a sulfur atom. The term "aralkylthioalkyl" embraces aralkylthio radicals attached through a sulfur atom to an alkyl radical. The term "aminoalkyl" embraces alkyl radicals substituted with amino radicals. More preferred are "lower aminoalkyl" radicals. Examples of such radicals include aminomethyl, aminoethyl, and the like. The term "alkylamino" denotes amino groups which have been substituted with one or two alkyl radicals. Preferred are "lower N-alkylamino" radicals having alkyl portions having 1 to 6 carbon atoms. Suitable lower alkylamino may be mono or dialkylamino such as N-methylamino, N-ethylamino, N,N-dimethylamino, N,N-diethylamino or the like. The term "arylamino" denotes amino groups which have been substituted with one or two aryl radicals, such as N-phenylamino. The "arylamino" radicals may be further substituted on the aryl ring portion of the radical. The term "aralkylamino" embraces aralkyl radicals attached through an nitrogen atom to other radicals. The terms "N-arylaminoalkyl" and "N-aryl-N-alkyl-aminoalkyl" denote amino groups which have been substituted with one aryl radical or one aryl and one alkyl radical, respectively, and having the amino group attached to an alkyl radical. Examples of such radicals include N-phenylaminomethyl and N-phenyl-N-methylaminomethyl. The term "aminocarbonyl" denotes an amide group of the formula —C(=O) NH$_2$. The term "alkylaminocarbonyl" denotes an aminocarbonyl group which has been substituted with one or two alkyl radicals on the amino nitrogen atom. Preferred are "N-alkylaminocarbonyl" "N,N-dialkylaminocarbonyl" radicals. More preferred are "lower N-alkylaminocarbonyl" "lower N,N-dialkylaminocarbonyl" radicals with lower alkyl portions as defined above. The term "alkylaminoalkyl" embraces radicals having one or more alkyl radicals attached to an aminoalkyl radical. The term "aryloxyalkyl" embraces radicals having an aryl radicals attached to an alkyl radical through a divalent oxygen atom. The term "arylthioalkyl" embraces radicals having an aryl radicals attached to an alkyl radical through a divalent sulfur atom.

Also included in the family of compounds of Formula I are the pharmaceutically-acceptable salts thereof. The term pharmaceutically-acceptable salts embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclo, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicylic, galactaric and galacturonic acid. Suitable pharmaceutically-acceptable base addition salts of compounds of Formula I include metallic salts made from aluminum calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The cyclooxygenase-2 inhibitor compounds of the invention can be synthesized according to the following procedures of Schemes I–XV, wherein the R$^1$–R$^3$ substituents are as defined for Formula I, above, except where further noted.

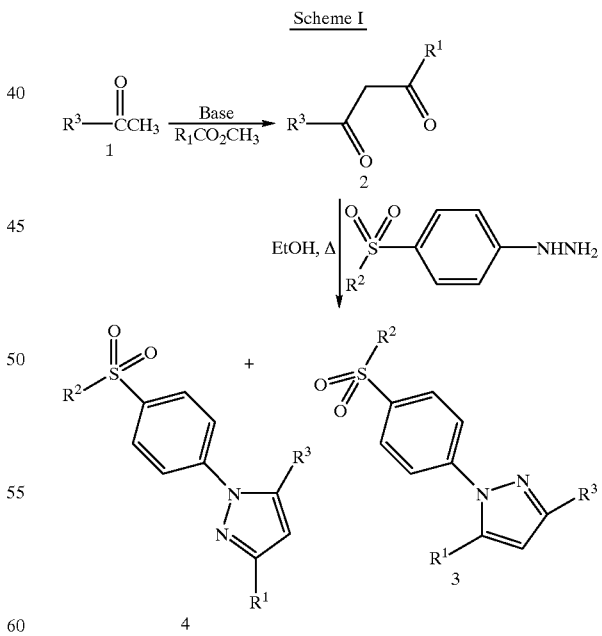

Synthetic Scheme I shows the preparation of cyclooxygenase-2 inhibitor compounds, as described in WO95/15316 and U.S. Pat. No. 5,466,823, which are incorporated by reference. In step 1, ketone 1 is treated with a base, preferably NaOMe or NaH, and an ester, or ester equivalent, to form the intermediate diketone 2 (in the enol form) which is used without further purification. In step 2, diketone 2 in an anhydrous protic solvent, such as absolute ethanol or acetic acid, is treated with the hydrochoride salt or the free base of a substituted hydrazine at reflux to afford a mixture of pyrazoles 3 and 4. Recrystallization or chromatography affords 3 usually as a solid. Similar pyrazoles can be prepared by methods described in U.S. Pat. Nos. 5,401,765, 5,434,178, 4,146,721, 5,051,518, 5,134,142 and 4,914,121 that also are incorporated by reference.

Scheme II

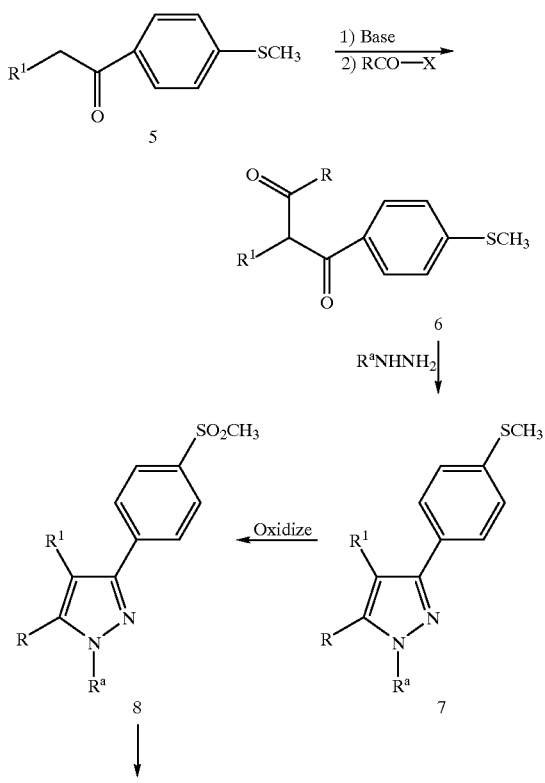

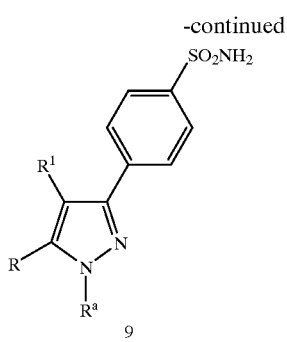

Scheme II shows the four step procedure for forming cyclooxygenase-2 inhibitor pyrazoles 8 as described in U.S. Pat. No. 5,486,534, which is incorporated by reference, (where $R^a$ is hydrido or alkyl) from ketones 5. In step 1, ketone 5 is reacted with a base, such as lithium bis (trimethylsilyl) amide or lithium diisopropylamide (LDA) to form the anion. In step 2, the anion is reacted with an acetylating reagent to provide diketone 6. In step 3, the reaction of diketone 6 with hydrazine or a substituted hydrazine, gives pyrazole 7. In step 4, the pyrazole 7 is oxidized with an oxidizing reagent, such as Oxone® (potassium peroxymonosulfate), 3-chloroperbenzoic acid (MCPBA) or hydrogen peroxide, to give a mixture of the desired 3-(alkylsulfonyl)phenyl-pyrazole 8 and the 5-(alkylsulfonyl)phenyl-pyrazole isomer. Sulfonamides 9 can be prepared such as by the Huang method [*Tet. Lett.*, 35, 7201–04 (1994)].

Alternatively, diketone 6 can be formed from ketone 5 by treatment with a base, such as sodium hydride, in a solvent, such as dimethylformamide, and further reacting with a nitrile to form an aminoketone. Treatment of the aminoketone with acid forms the diketone 6. Similar pyrazoles can be prepared by methods described in U.S. Pat. No. 3,984,431 which is incorporated by reference.

Scheme III

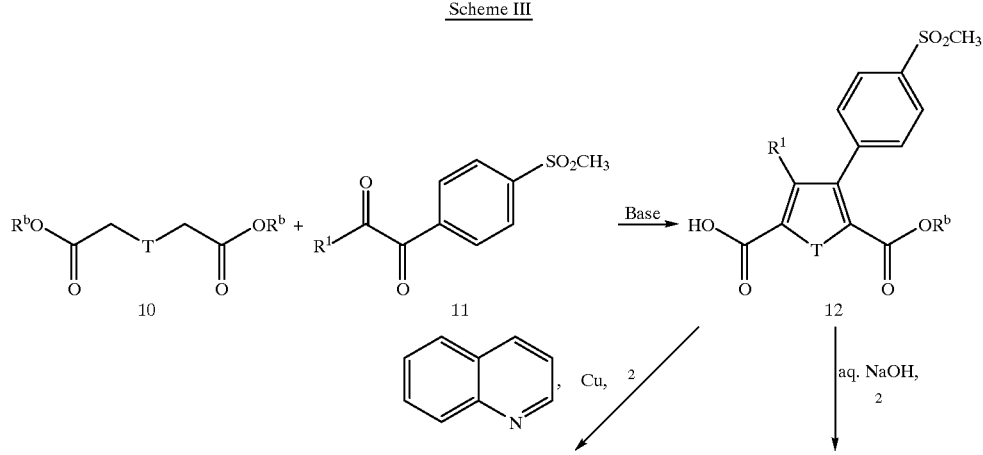

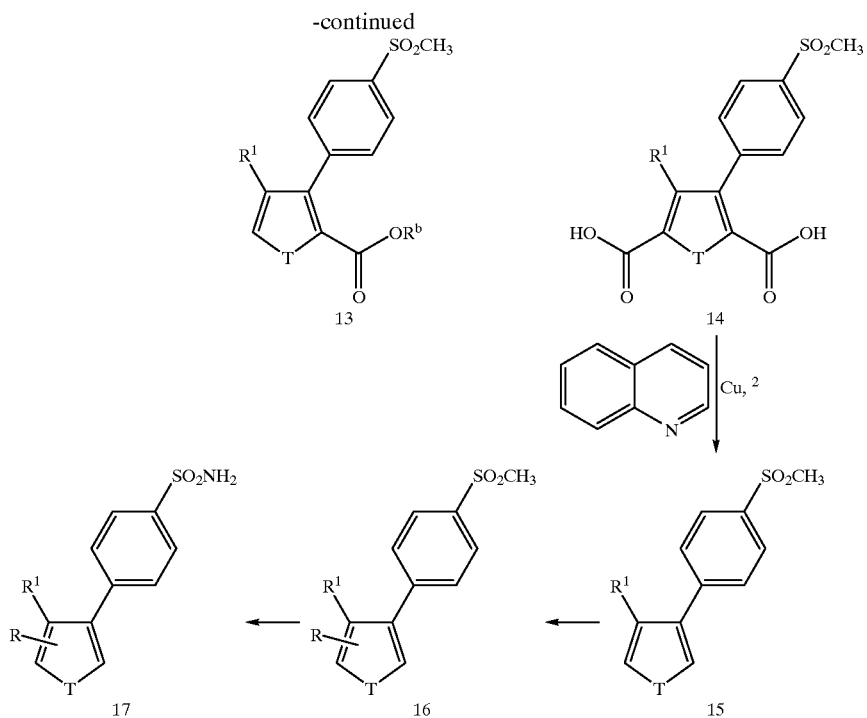

Cyclooxygenase-2 inhibitor diaryl/heteroaryl thiophenes (where T is S, and $R^b$ is alkyl) can be prepared by the methods described in U.S. Pat. Nos. 4,427,693, 4,302,461, 4,381,311, 4,590,205, and 4,820,827, and PCT documents WO 95/00501 and WO94/15932, which are incorporated by reference. Similar pyrroles (where T is N), furanones and furans (where T is O) can be prepared by methods described in PCT documents WO 95/00501 and WO94/15932.

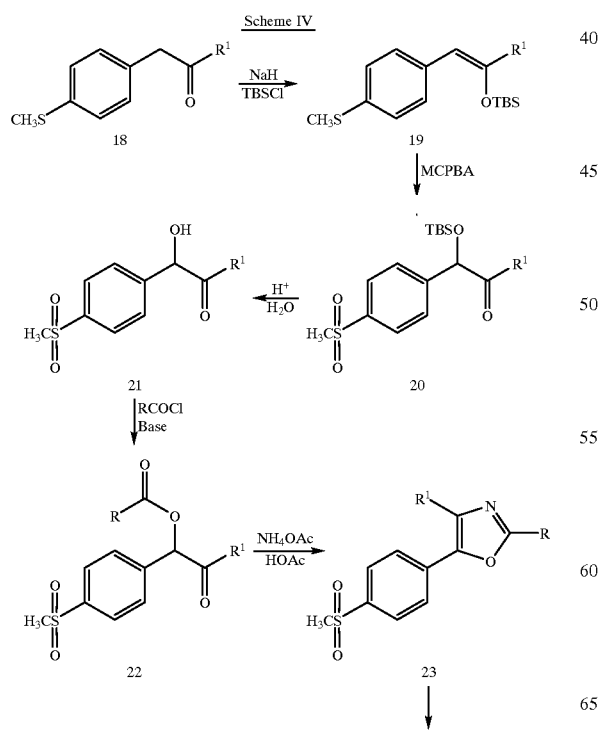

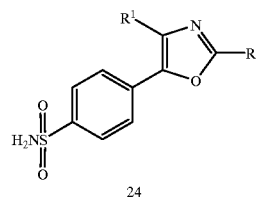

Cyclooxygenase-2 inhibitor diaryl/heteroaryl oxazoles can be prepared by the methods described in U.S. Pat. Nos. 5,380,738, 3,743,656, 3,644,499 and 3,647,858, and PCT documents WO 95/00501 and WO94/27980, which are incorporated by reference

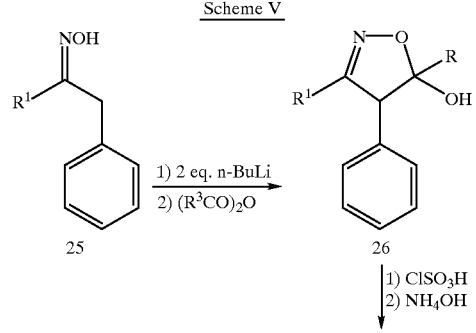

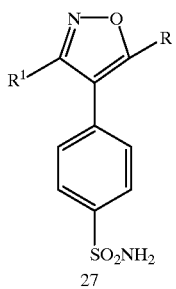

Cyclooxygenase-2 inhibitor diaryl/heteroaryl isoxazoles can be pre-oared by the methods described in PCT application Ser. No. US96/01869, PCT documents WO92/05162, and WO92/19604, and European Publication EP 26928, which are incorporated by reference. Sulfonamides 27 can be formed from the hydrated isoxazole 26 in a two step procedure. First, hydrated i-soxazole 26 is treated at about 0° C. with two or three equivalents of chlorosulfonic acid to form the corresponding sulfonyl chloride. In step two, the sulfonyl chloride thus formed is treated with concentrated ammonia to provide the sulfonamide derivative 27.

such as trimethylaluminum, trimethylaluminum, dimethylaluminum chloride, diethylaluminum chloride in the presence of inert solvents such as toluene, benzene, and xylene, gives amidines 30. In step 2, the reaction of amidine 30 with 2-haloketones (where X is Br or Cl) in the presence of bases, such as sodium bicarbonate, potassium carbonate, sodium carbonate, potassium bicarbonate or hindered tertiary amines such as N,N'-diisopropylethylamine, gives the 4,5-dihydroimidazoles 31 (where $R^b$ is alkyl). Some of the suitable solvents for this reaction are isopropanol, acetone and dimethylformamide. The reaction may be carried out at temperatures of about 20° C. to about 90° C. In step 3, the 4,5-dihydroimidazoles 31 may be dehydrated in the presence of an acid catalyst such as 4-toluenesulfonic acid or mineral acids to form the 1,2-disubstituted imidazoles 32 of the invention. Suitable solvents for this dehydration step are e.g., toluene, xylene and benzene. Trifluoroacetic acid can be used as solvent and catalyst for this dehydration step. Sulfonamides 33 can be prepared such as by the Huang method [*Tet. Lett.*, 35, 7201–04 (1994)].

In some cases (e.g., where R=methyl or phenyl) the intermediate 31 may not be readily isolable. The reaction, under the conditions described above, proceeds to give the targeted imidazoles directly.

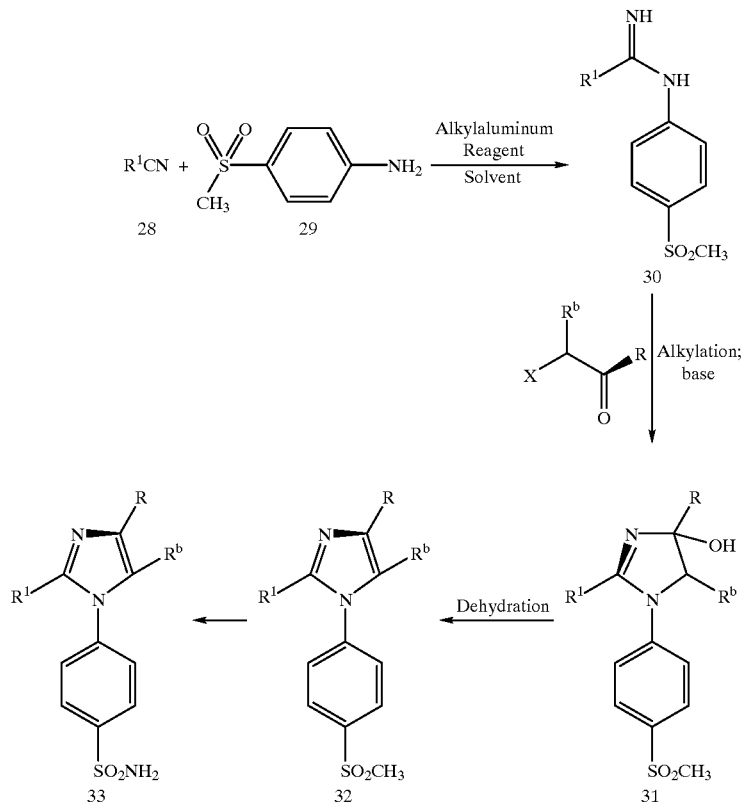

Scheme VI shows a three step preparation of the cyclooxygenase-2 inhibitor imidazoles 33. In step 1, the reaction of substituted nitrites ($R^1CN$) 28 with primary phenylamines 29 in the presence of alkylaluminum reagents Similarly, imidazoles can be prepared having the sulfonylphenyl moiety attached at position 2 and $R^1$ attached at the nitrogen atom at position 1. Diaryl/heteroaryl imidazoles can be prepared by the methods described in U.S. Pat. Nos.

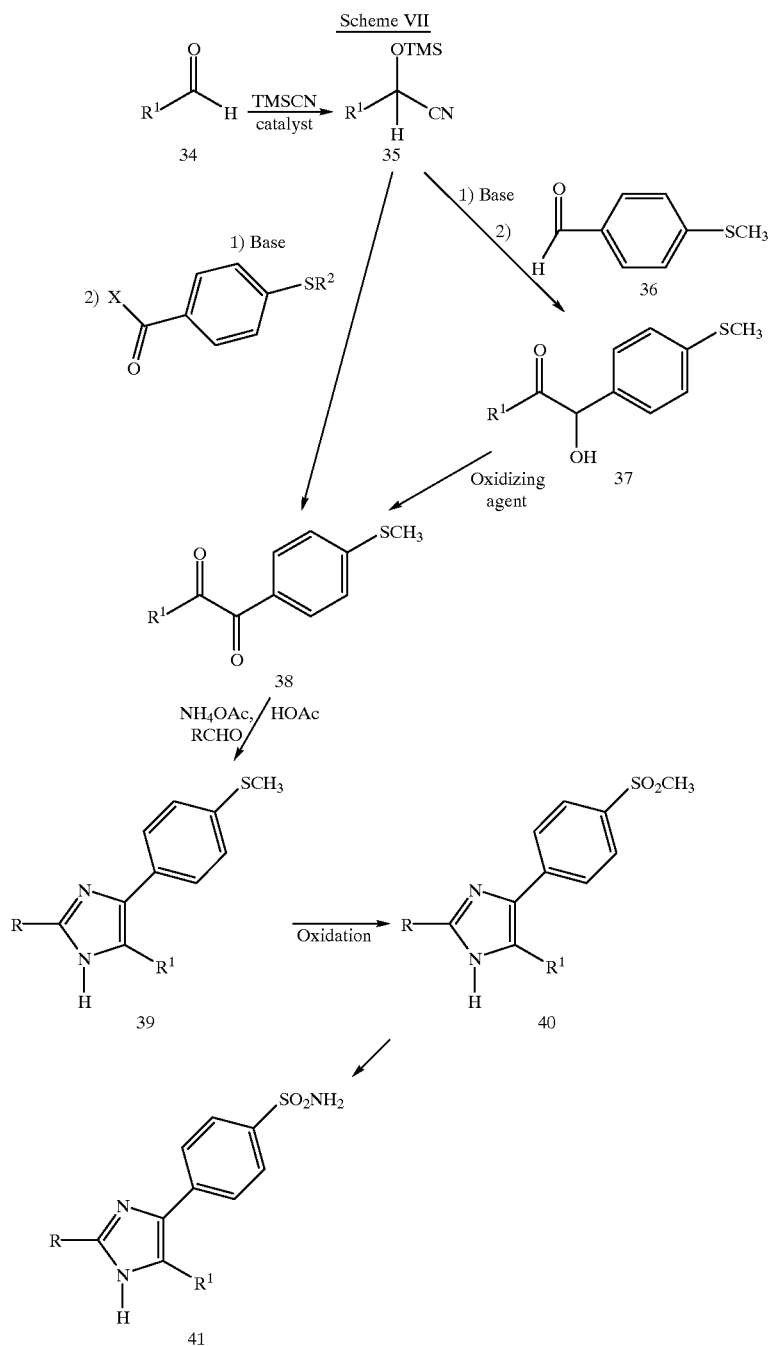

Scheme VII

Imidazole cyclooxygenase-2 inhibitor compounds 41 may be synthesized according to the sequence outlined in Scheme VII. Aldehyde 34 may be converted to the protected cyanohydrin 35 by reaction with a trialkylsilyl cyanide, such as trimethylsilyl cyanide (TMSCN) in the presence of a catalyst such as zinc iodide ($ZnI_2$) or potassium cyanide (KCN). Reaction of cyanohydrin 35 with a strong base followed by treatment with benzaldehyde 36 and using both acid and base treatments, in that order, on workup gives benzoin 37. Examples of strong bases suitable for this reaction are lithium diisopropylamide (LDA) and lithium hexamethyldisilazane. Benzoin 37 may be converted to benzil 38 by reaction with a suitable oxidizing agent, such as bismuth oxide or manganese dioxide, or by a Swern oxidation using dimethyl sulfoxide (DMSO) and trifluoroacetic anhydride. Benzil 38 may be obtained directly by reaction of the anion of cyanohydrin 35 with a substituted benzoic acid halide. Any of compounds 37 and 38 may be used as intermediates for conversion to imidazoles 39 according to chemical procedures known by those skilled in the art and described by M. R. Grimmett, "Advances in Imidazole Chemistry" in Advances in Heterocyclic Chemistry, 12, 104 (1970). The conversion of 38 to imidazoles 39 is carried out by reaction with ammonium acetate and an appropriate aldehyde (RCHO) in acetic acid. Benzoin 37 may be converted to imidazoles 39 by reaction with formamide. In addition, benzoin 37 may be converted to imidazoles by first acylating with an appropriate acyl group (RCO—) and then treating with ammonium hydroxide. Those skilled in the art will recognize that the oxidation of the sulfide to the sulfone may be carried out at any point along the way beginning with compounds 36, and including oxidation of imidazoles 39, using, for examples, reagents such as hydrogen peroxide in acetic acid, m-chloroperoxybenzoic acid (MCPBA) and potassium peroxymonosulfate (OXONE®). Sulfonamides 41 can be prepared such as by the Huang method [*Tet. Lett.*, 35, 7201–04 (1994)].

Diaryl/heteroaryl imidazoles can be prepared by the methods described in U.S. Pat. Nos. 3,707,475, 4,686,231, 4,503,065, 4,472,422, 4,372,964, 4,576,958, 3,901,908, PCT application Serial No. US95/0505, European publication EP 372,445, and PCT document WO 95/00501, which are incorporated by reference.

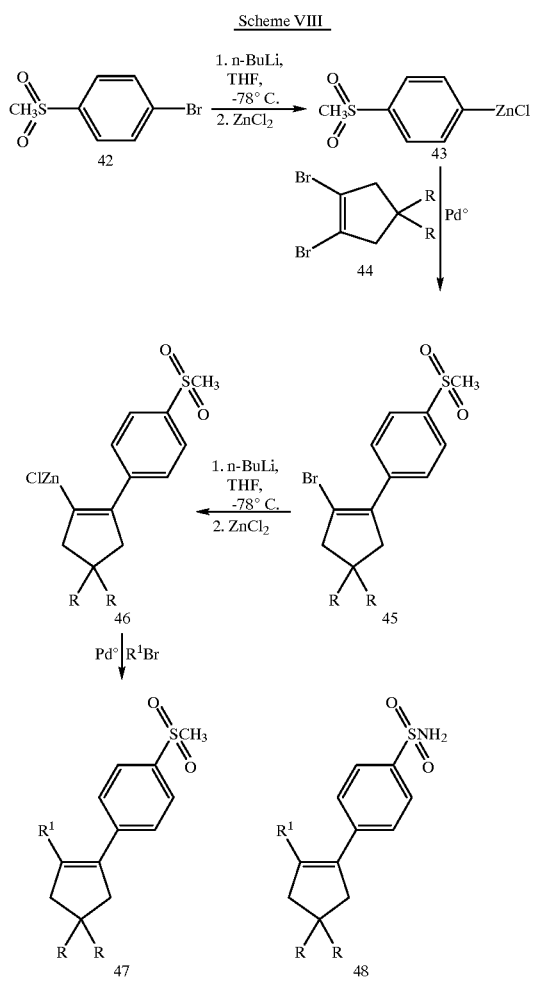

Diaryl/heteroaryl cyclopentene cyclooxygenase-2 inhibitors can be prepared by the methods described in U.S. Pat. No. 5,344,991, and PCT document WO 95/00501, which are incorporated by reference.

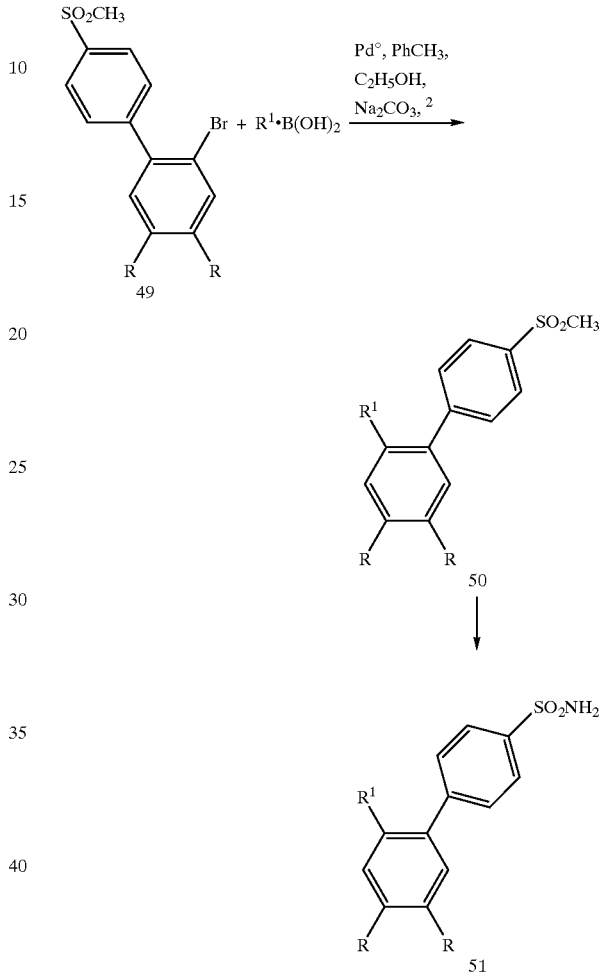

Similarly, Synthetic Scheme IX shows the procedure for the preparation of 1,2-diarylbenzene cyclooxygenase-2 inhibitor agents 51 from 2-bromo-bipohenyl intermediates 49 (prepared similar to that described in Synthetic Scheme VIII) and the appropriate substituted phenylboronic acids. Using a coupling procedure similar to the one developed by Suzuki et al. [*Synth. Commun.*, 11, 513 (1981)], intermediates 49 are reacted with the boronic acids in toluene/ethanol at reflux in the presence of a Pd° catalyst, e.g., tetrakis (triphenylphosphine)palladium(0), and 2 M sodium carbonate to give the corresponding 1,2-diarylbenzene antiinflammnatory agents 50 of this invention. Sulfonamides 51 can be prepared such as by the Huang method [*Tet. Lett*, 35, 7201–04 (1994)]. Such terphenyl compounds can be prepared by the methods described in U.S. application Ser. No. 08/346,433, which is incorporated by reference.

Scheme X

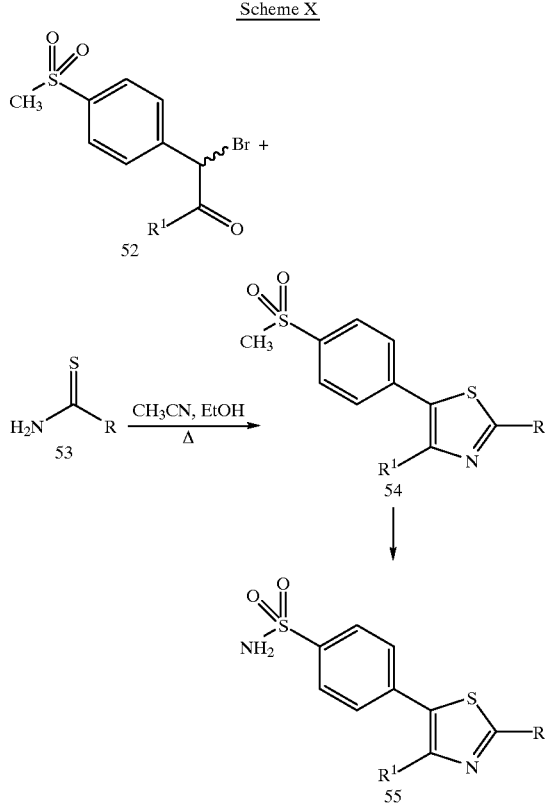

Diaryl/heteroaryl thiazole cyclooxygenase-2 inhibitors can be prepared by the methods described in U.S. Pat. No. 4,051,250, 4,632,930, European document EP 592,664, and PCT documents WO96/03392, and WO 95/00501, which are incorporated by reference. Isothiazoles can be prepared as described in PCT document WO 95/00501.

Diaryl/heteroaryl pyridine cyclooxygenase-2 inhibitors can be prepared by the methods described in U.S. Pat. Nos. 5,169,857, 4,011,328, 4,533,666, PCT application Ser. No. US96/01110 and PCT application Ser. No. US96/01111, which are incorporated by reference.

The radiolabeled compounds can be prepared by methods which are known per se for related compounds by using readily available radiolabelled synthons like [C-11]CO$_2$, [C-11]CH$_3$I, [C-11]HCN, [C-11]CO, [F-18]F$_2$, [F-18]KF, [F-18]CH$_3$CO$_2$F and [I-123]NaI. The preparation of precursors for labeled agents are described in the Examples. The position of the radiolabel in the agent is not relevant and can be chosen according to the ease of synthesizing the agent. Selenium-73 can be introduced as a radioactive label into the agent by substituting a mercapto group by a $^{73}$Se-H group. Radioactive halogen can be substituted for one of the hydrogen atoms at choice in the precursor.

The labeled cyclooxygenase-2 specific agents of the invention can be synthesized according to the following procedures of Schemes XI–XV.

Scheme XI

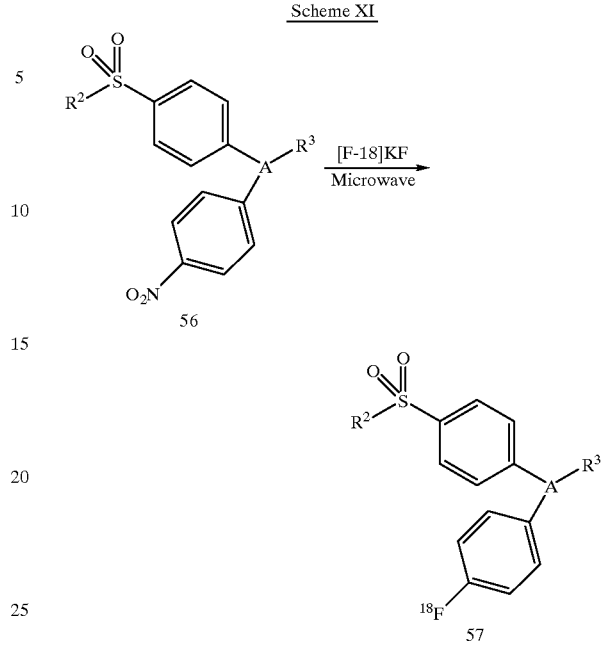

Synthetic Scheme XI shows the procedure for the preparation of labeled cyclooxygenase-2 inhibitor agents 57 from nitro-substituted compounds 56. An appropriately substituted or unsubstituted aromatic nitro compound such as 56 can be treated with an organic soluble source of the $^{18}$F isotope using microwave-assisted halide exchange, to give the corresponding labeled agents 57 of this invention. The organic soluble source can be such complexes as kryptofix [2.2.2] potassium fluoride, tetra-n-butylammonium fluoride, 18-crown-6 potassium fluoride complex and the like. The aromatic nitro compound is normally treated with the organic soluble fluoride source in a suitable dipolar aprotic organic solvent such as dimethylsulfoxide (DMSO), dimethyl acetamide (DMAC), or dimethyformaminde (DMF) to effect nitro for fluoro exchange. The aromatic nitro compound can be an ortho or para-nitro phenyl or substituted ortho or para-nitro derivative. Selected heterocyclic Nitro compounds can also be substituted with $^{18}$F, such as nitropyridine isomers, nitrothiophene and the like.

Scheme XII

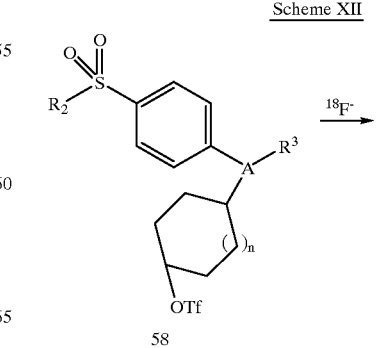

-continued

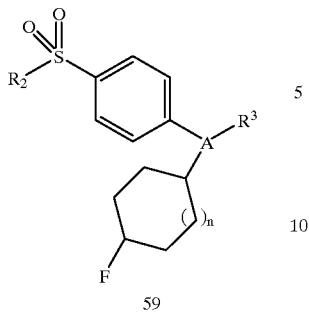

59

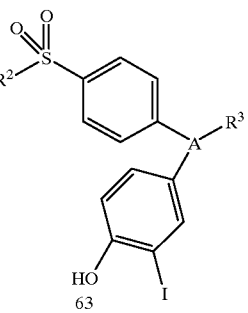

63

Aliphatic $^{18}F$ analogs for PET study may also be prepared by displacement of appropriately activated cycloalkyl derivatives. For example, a cycloalkyl triflate 58 can be converted to the corresponding cycloalkyl fluoro derivative 59 upon treatment with a suitable organic soluble source of $^{18}F$ as described above. In addition to analogs 57 and 59, water soluble pro-drug derivatives can also be prepared for administration by injection.

Radioiodinated ($^{125}I$ or $^{123}I$) agents for COX-2 visualization may be prepared by displacement of appropriate phenol derivatives. For example, radioiodination can be performed by adding sodium ($^{125}I$) iodide to the hydroxyphenyl compound in the presence of an oxidizing agent (such as sodium hypochlorite, chloramine T, dichloramine t, hydrogen peroxide, peroxyacetic acid and iodine)

Scheme XIII

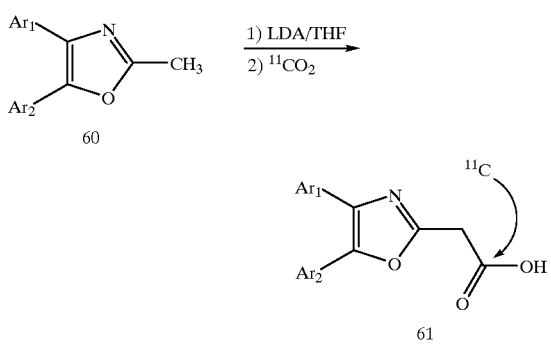

Incorporation of $^{11}C$ into COX-2 inhibitors for PET applications can be from $^{11}CO_2$. Condensation of $^{11}CO_2$ with an anionic form of a typical COX-2 inhibitor will provide the corresponding isotopically labeled carboxylic acid. The acid may be used as an inhibitor or may be converted into another compound by conventional organic reactions. A wide variety of analogs can be prepared by this method so long as the synthesis is conducted in a rapid manner. The anion of the COX-2 selective inhibitor is generated with a strong base such as n-butyllithium or lithium diisopropyl amide (LDA) and then treated with $^{11}CO_2$ that has been dried to remove any moisture.

Scheme XIV

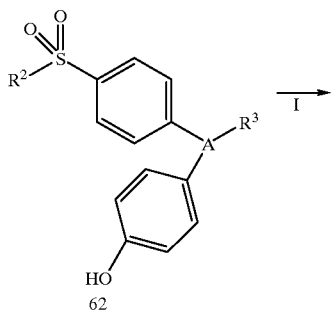

Scheme XV

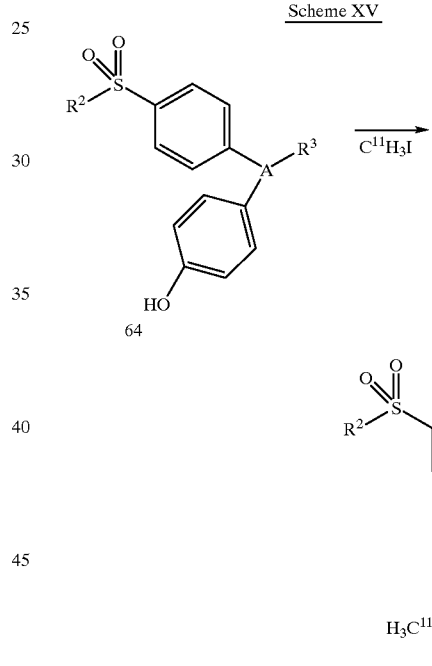

Labeled ($^{11}C$) agents for COX-2 visualization may be prepared by displacement of appropriate phenol derivatives. For example, the hydroxyl-substituted phenyl ring can be methylated by adding ($^{11}C$) methyl iodide.

The references recited herein are incorporated by reference.

The following examples contain detailed descriptions of the methods of preparation of compounds of Formula I. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in degrees Centigrade unless otherwise indicated.

EXAMPLE 1

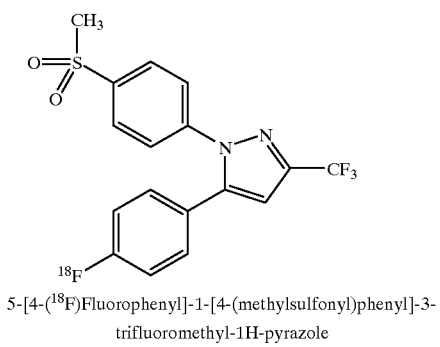

5-[4-($^{18}$F)Fluorophenyl]-1-[4-(methylsulfonyl)phenyl]-3-trifluoromethyl-1H-pyrazole Step 1. Preparation of 1-[4-(methylsulfonyl)phenyl]-5-(4-nitrophenyl)-3-trifluoromethyl-1H-pyrazole.

4-Methylsulfonylphenylhydrazine hydrochloride (882 mg, 3.96 mmol) and 4,4,4-trifluoromethyl-1-(4-nitrophenyl)-butane-1,3-dione (950 mg, 3.6 mmol) were dissolved in 20 ml of absolute ethanol and heated to reflux for 4 hours. The solution was cooled to room temperature, diluted with 20 mL of water and let stand, whereupon crystals formed that were isolated by filtration to provide 1-[4-(methylsulfonyl)phenyl]-5-(4-nitrophenyl)-3-trifluoromethyl-1H-pyrazole (1.2 g, 81%): mp 203–205° C. $^1$H NMR (DMSO-$d_6$/300 MHz) 8.24 (d, J=8.70 Hz, 2 H), 8.01 (d, J=8.70 Hz, 2 H), 7.65 (d, J=8.70 Hz, 2 H), 7.61 (d, J=8.70 Hz, 2 H), 7.44 (s, 1 H), 3.23 (s, 3 H). Anal. calc'd. for $C_{17}H_{12}F_3N_3O_4S$: C, 49.64; H, 2.94; N, 10.21. Found: C, 49.59; H, 2.94; N, 10.21.

Step 2. Preparation of 5-[4-($^{18}$F)fluorophenyl]-1-[4-(methylsulfonyl)phenyl]-3-trifluoromethyl-1H-pyrazole.

1-[4-(Methylsulfonyl)phenyl]-5-(4-nitrophenyl)-3-trifluoromethyl-1H-pyrazole (Step 1) was radiolabeled with $^{18}$F-via microwave assisted nitro to fluoro exchange (5 minutes) as described in General Synthetic Scheme XI to form 5-[4-($^{18}$F)fluorophenyl]-1-[4-(methylsulfonyl) phenyl]-3-trifluoromethyl-1H-pyrazole. Purification by silica gel HPLC yielded the desired pyrazole in 20–30% yield.

EXAMPLE 2

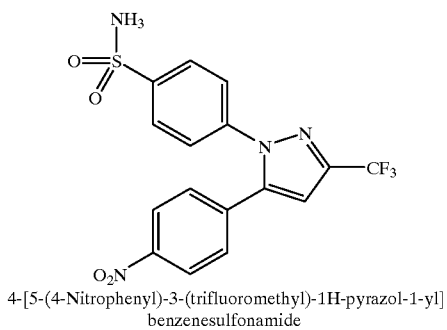

4-[5-(4-Nitrophenyl)-3-(trifluoromethyl)-1H-pyrazol-1-yl]benzenesulfonamide

Step 1. Preparation of 4,4,4-trifluoromethyl-1-[4-nitrophenyl]-butane-1,3-dione.

Ethyl trifluoroacetate (15.9 g, 0.133 mol) and 4-nitroacetophenone (20.0 g, 0.121 mol) were diluted with 60 mL, of ether. The stirred solution was treated with 25 weight % sodium methoxide in methanol (65 mL, 0.302 mol). The mixture was stirred at room temperature for 16 hours and treated with 40 mL of concentrated hydrochloric acid. The solution was diluted with 80 mL of water and the phases separated. The ethereal solution was washed with brine, dried over anhydrous $MgSO_4$, filtered and concentrated in vacuo to afford a yellow solid that was used directly in the next step without further purification (6.07 g, 19%).

Step 2. Preparation of 4-[5-(4-nitrophenyl)-3-(trifluoromethyl)-1H-pyrazol-1-yl]benzenesulfonamide.

4-Sulfonamidophenylhydrazine hydrochloride (886 mg, 3.96 mmol) and 4,4,4-trifluoromethyl-1-[4-nitrophenyl]-butane-1,3-dione (950 mg, 3.6 mmol) were dissolved in 20 mL of absolute ethanol and heated to reflux for 4 hours. The solution was cooled to room temperature, diluted with 20 mL of water and let stand, whereupon crystals formed that were isolated by filtration to provide 4-[5-(4-nitrophenyl)-3-(trifluoromethyl)-1H-pyrazol-1-yl]benzenesulfonamide (800 mg, 54%): mp 173–175° C. $^1$H NMR (DMSO-$d_6$/300 MHz) 8.24 (d, J=8.85 Hz, 2 H), 7.88 (d, J=8.25 Hz, 2 H), 7.60 (d, J=8.85 Hz, 2 H), 7.57 (d, J=8.25 Hz, 2 H), 7.52 (brs, 2 H), 7.44 (s, 1 H).

Anal. calc'd. for $C_{16}H_{11}F_3N_4O_4S$: C, 44.61; H, 2.69; N, 13.59.

Found: C, 46.53; H, 2.71; N, 13.48.

EXAMPLE 3

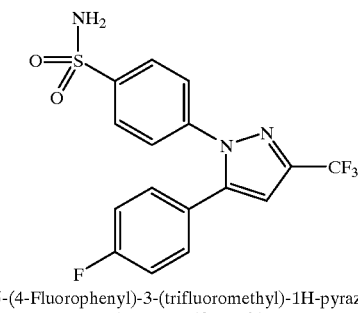

4-[5-(4-Fluorophenyl)-3-(trifluoromethyl)-1H-pyrazol-1-yl]benzenesulfonamide

4-Sulfonamidophenylhydrazine hydrochloride (980 mg, 4.4 mmol) and 4,4,4-trifluoromethyl-1-(4-fluorophenyl)-butane-1,3-dione (1.04 g, 4.0 mmol) were dissolved in 100 mL of absolute ethanol and heated to reflux for 16 hours. The solution was cooled to room temperature and diluted with 80 mL of water whereupon crystals of pure 4-[5-(4-fluorophenyl)-3-(trifluoromethyl)-1H-pyrazol-1-yl]benzenesulfonamide formed that were isolated by filtration and air dried (1.30 g, 84%): mp 165–166° C. $^1$H NMR (DMSO-$d_6$/300 HMz) 7.88 (d, J=8.70 Hz, 2 H), 7.57–7.52 (m, 4 H), 7.40–7.35 (m, 2 H), 7.29–7.22 (m, 3 H). $^{19}$NMR ($CDCl_3$) −61.36, −111.87. Anal. calc'd. for $C_{16}H_{11}F_4N_3O_2S$: C, 49.87; H, 2.88; N, 10.90. Found: C, 49.75; H, 2.82; N, 10.84.

EXAMPLE 4

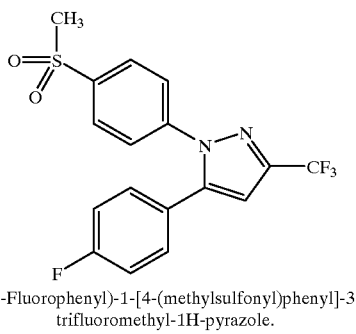

5-(4-Fluorophenyl)-1-[4-(methylsulfonyl)phenyl]-3-trifluoromethyl-1H-pyrazole.

4-Methylsulfonylphenylhydrazine hydrochloride (2.45 g, 0.011 mmol) and 4,4,4-trifluoromethyl-1-(4-fluorophenyl)-butane-1,3-dione (2.61 g, 0.01 mmol) were dissolved in 100 mL of absolute ethanol and heated to reflux for 16 hours. The solution was cooled to room temperature and diluted with 100 mL of water, whereupon crystals of pure 5-(4-fluorophenyl)-1-[4-(methylsulfonyl)phenyl]-3-trifluoromethyl-1H-pyrazole formed that were isolated by filtration and air dried (3.60 g, 94%): mp 127–129° C. $^1$H NMR (DMSO-D$_6$/300 MHz) 8.00 (d, J=8.70 Hz, 2 H), 7.60 (d, J=8.70 Hz, 2 H), 7.41–7.36 (m, 2 H), 7.29–7.23 (m, 3 H), 3.23 (s, 3 H). $^{19}$F NMR (CDCl$_3$) –61.42, –111.77. Anal. calc'd. for C$_{17}$H$_{12}$F$_4$N$_2$O$_2$S: C, 53.12; r: 3.15; N, 7.29. Found: C, 53.22; H, 3.18; N, 7.27.

EXAMPLE 5

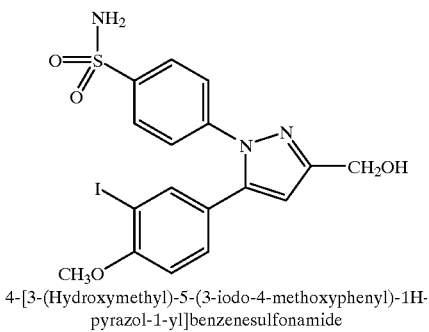

4-[3-(Hydroxymethyl)-5-(3-iodo-4-methoxyphenyl)-1H-pyrazol-1-yl]benzenesulfonamide Step 1. Preparation of methyl [1-(4-aminosulfonylphenyl)-5-(4-benzyloxyphenyl)-1H-pyrazol-3-yl]carboxylate.

Dimethyl oxalate (2.83 g, 24 mmol) and 4'-benzyloxyacetoohenone (5.00 g, 22 mmol) were dissolved in a mixture of ether (20 mL) and methanol (40 mL), and treated with 25% sodium methoxide in methanol (5.19 g, 24 mmol). The mixture was stirred at room temperature for 16 hours, diluted with 3 N HCl and extracted with ether. The ethereal solution was washed with water, dried over anhyd. MgSO$_4$, filtered and concentrated in vacuo to afford a solid. The crude solid was dissolved in absolute ethanol (150 mL), combined with 4-sulfonamidophenylhydrazine hydrochloride (5.37 g, 24 mmol) and heated to reflux for 16 hours. The solution was diluted with water (50 mL) and cooled to room temperature, whereupon crystals formed that were isolated by filtration and air dried to afford the title compound as a light yellow solid (9.78 g, 93%): mp 218.0–219.4° C. $^1$H NMR (Acetone-d$_6$) 7.95 (d, 2 H, J=8.7 Hz), 7.55 (d, 2 H, J=8.7 Hz), 7.51 (d, 2 H, J=6.9 Hz), 7.46–7.31 (m, 3 H), 7.27 (d, 2H, J=8.7 Hz), 7.05 (d 2 H, J=8.7 Hz), 7.00 (s, 1 H), 6.75 (br s, 2 H), 5.16 (S, 2 H), 4.37 (G, 2 H, J=7.2 Hz), 1.37 (t, 3 H, J=7.2 Hz). FABHRMS m/z 478.1426 (M+H, C$_{25}$H$_{24}$N$_3$O$_5$S calc'd 478.1437).

Step 2. Preparation of 4-[5-(4-benzyloxyphenyl)-3-(hydroxymethyl)-1H-pyrazol-1-yl]benzenesulfonamide.

The pyrazole from Step 1 (2.00 g, 4.2 mmol) was dissolved in THF (100 mL) under nitrogen and treated with 10 M borane in THF (1.7 mL, 17 mmol) dropwise at room temperature. The reaction mixture was heated to reflux for 16 hours, cooled to room temperature and treated with absolute ethanol. The solution was diluted with water, and extracted with ethyl acetate. The combined extracts were washed with brine, dried over anhyd. MgSO$_4$, filtered and concentrated in vacuo to afford a solid that was crystallized from aqueous ethanol to afford the title compound as a white solid (1.50 g, 82%): mp 196.4–197.7° C. $^1$H NMR (Acetone-d$_6$) 7.87 (d, 2 H, J=8.7 Hz), 7.53–7.30 (m, 7.H), 7.23 (d, 2 H, J=8.7 Hz), 7.05 (d, 2 H, J=6.9 Hz), 6.68 (br s, 2 H), 6.55 (s, 1 H), 5.16 (s, 2 H), 4.66 (d, 2 H:, J=5.7 Hz), 4.21 (t, 1 H, J=5.7 Hz). FABHRMS m/z 436.1322 (M+H, C$_{23}$H$_{22}$N$_3$O$_4$S calc'd 436.1331). Anal. Calc'd: C, 63.43; H, 4.86; N, 9.65. Found: C, 63.54; H, 4.87; N, 9.65.

Step 3. Preparation of 4-[3-(hydroxymethyl)-5-(4-hydroxyphenyl)-1H-pyrazol-1-yl]benzenesulfonamide.

The compound from Step 2 (22.43 g, 51.5 mmol) was dissolved in dichloromethane (300 mL) under nitrogen, cooled to –78° C. and treated with 1.0 M boron trichloride in dichloromethane (100 mL, 0.1 mol). The solution was warmed to 0° C., cooled to –78° C., treated with 30 mL of methanol and warmed to room temperature. The solution was concentrated in vacuo, and the residue was crystallized from ethyl acetate/hexanes to afford the title compound as a white solid (17.50 g, 98%): mp 194.6–198.1° C. $^1$H NMR (Acetone-d$_6$) 8.71 (br s 1 H), 7.87 (d, 2 H, J=8.7 Hz), 7.46 (d, 2 H, J=8.7 Hz), 7.13 (d, 2 H, J=8.4 Hz), 6.85 (d, 2 H, J=8.4 Hz), 6.66 (br s, 2 H), 6.51 (s, 1 H), 4.65 (s, 2 H).

Step 4. Preparation of 4-[3-(hydroxymethyl)-5-(4-hydroxy-3-iodo-phenyl)-1H-pyrazol-1-yl]benzenesulfonamide.

A mixture of the compound from Step 3 (5.00 g, 14.5 mmol), sodium iodide (2.20 g, 14.5 mmol), 2.5 N sodium hydroxide (5.8 mL, 14.5 mmol) and methanol (60 mL) was cooled to 0° C. and treated dropwise with 5% aqueous sodium hypochlorite (commercial bleach) (22 mL, 14.5 mmol). The solution was warmed to room temperature and stirred for 3 hours. The pH was adjusted to 7 by the addition of 1 N HCl, and the solution was diluted with 25 mL of water, whereupon crystals formed that were isolated by filtration and air dried to afford the title compound as a white solid (4.50 g, 66%): mp 243.2–245.2° C. $^1$H NMR (Acetone-d$_6$) 9.50 (br s 1 H), 7.90 (d, 2 H, J=8.7 Hz), 7.74 (d, 1 H, J=2.4 Hz), 7.48 (d, 2 H, J=8.7 Hz), 7.08 (dd, 1 H, J=8.4, 2.4 Hz), 6.93 (d, 1 H, J=8.4 Hz), 6.68 (br s, 2 H), 6.58 (s, 1 H), 4.66 (s, 2 H), 4.20 (br s, 1 H). FABHRMS m/z 471.9791 (M+, C$_{16}$H$_{14}$IN$_3$O$_4$S calc'd 471.9828).

Step 5. Preparation of 4-[3-(hydroxymethyl)-5-(3-iodo-4-methoxyphenyl)-1H-pyrazol-1-yl]benzenesulfonamide.

A solution of the compound from Step 4 (1.50 g, 3.2 mmol) in 100 mL of acetone was stirred with potassium carbonate (1.33 g, 9.6 mol) and methyl iodide (0.45 g, 3.2 mmol) at room temperature for 16 hours. The mixture was diluted with ethyl acetate, washed with 1 N HCl, brine, dried over anhyd. MgSO$_4$, filtered and concentrated in vacuo. The residue was purified by flash chromatography over silica gel (with 15/1 dichloromethane/methanol as eluant) and finally crystallized from aqueous ethanol to afford the title compound as a white solid (1.10 g, 71%): mp 192.3–193.3° C. $^1$H NMR (Acetone-d$_6$) 7.90 (d, 2 H, J=8.7 Hz), 7.78 (d, 1 H, J=1.8 Hz), 7.47 (d, 2 H, J=8.7 Hz), 7.23 (dd, 1 H, J=8.4, 1.8 Hz), 6.99 (d, 1 H, J=8.4 Hz), 6.66 (br s, 2 H), 6.59 (s, 1 H), 4.66 (s, 2 H), 4.20 (br s, 1 H). FABHRMS m/z 485.9975 (M+, $C_{17}H_{16}IN_3O_4S$ calc'd 485.9984). Anal. Calc'd: C, 42.07; H, 3.32; N, 8.66. Found: C, 42.17; H, 3.38; N, 8.57.

EXAMPLE 6

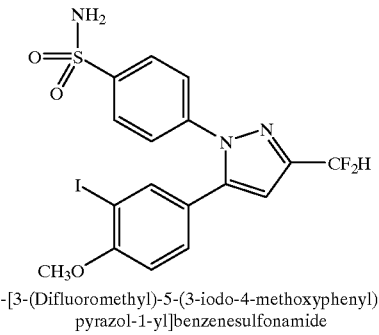

4-[3-(Difluoromethyl)-5-(3-iodo-4-methoxyphenyl)-1H-pyrazol-1-yl]benzenesulfonamide Step 1. Preparation of 4,4-difluoromethyl-1-(4-benzyloxyphenyl)-butane-1,3-dione.

Ethyl difluoroacetate (13.65 g, 0.11 mol) and 4'-benzyloxyacetophenone (22.63 g, 0.10 mol) were dissolved in 300 mL of ether, treated with 25% sodium methoxide in methanol (23.77 g, 0.11 mol) and stirred at room temperature for 16 hours. The solution was diluted with water, the phases separated, and the ethereal layer was dried over anhyd. $MgSO_4$, filtered and concentrated in vacuo to afford the title compound as a yellow solid (28.20 g, 93%): mrn 91.0–92.3° C.

Step 2. Preparation of 4-[5-(4-benzyloxyphenyl)-3-(difluoromethyl)-1H-pyrazol-1-yl]benzenesulfonamide.

A mixture of the dione from Step 1 (24.00 g, 78.9 mmol) and 4-Sulfonamidophenylhydrazine hydrochloride (19.41 g, 86.7 mmol) were dissolved in 300 mL of absolute ethanol and heated to reflux for 16 hours. The solution was cooled to room temperature and diluted with 300 mL of water whereupon a brown solid formed. The solid was isolated by filtration, washed with water and dried in vacuo to afford the title compound as a light tan solid (27.00 g, 75%): mp 135.2–137.4° C. $^1$H NMR (Acetone-$d_6$) 7.94 (d, 2 H, J=8.7 Hz), 7.53 (d, 2 H, J=8.7 Hz), 7.53–7.30 (m, 5 H), 7.28 (d, 2 H, J=8.7 Hz), 7.06 (d, 2 H, J=8.7 Hz), 6.94 (t, 1 H, J=54.4 Hz), 6.81 (s, 1 H), 6.71 (br s, 2 H), 5.16 (s, 2 H). Anal. Calcd for $C_{23}H_{19}F_2N_3O_3S$: C, 60.65; H, 4.20; N, 9.23. Found: C, 60.52; H, 4.17; N, 9.18.

Step 3. Preparation of 4-[3-(difluoromethyl)-5-(4-hydroxyphenyl)-1H-pyrazol-1-yl]benzenesulfonamide.

A solution of the pyrazole from Step 2 (24.50 g, 54 mmol) in 300 mL dichloromethane was cooled to –78°C. under nitrogen and treated with 1 M boron trichloride in dichloromethane (108 mL, 0.108 mol). The solution was warmed to 0° C. cooled to –78° C. and treated with 100 mL of methanol. The solution was warmed to room temperature and concentrated in vacuo. The residue was dissolved in methanol and concentrated in vacuo to afford a solid that was crystallized from aqueous ethanol to afford the title compound as a white solid (18.7 g, 95%) of: mp 188.8–190.8° C. $^1$H NMR (Acetone-$d_6$) 7.93 (d, 2 H, J=8.7 Hz), 7.52 (d, 2 H, J=8.7 Hz), 7.17 (d, 2 H, J=8.7 Hz), 6.93 (t, 1 H, J=54.9 Hz), 6.85 (d, 2 H, J=8.7 Hz), 6.77 (s, 1 H), 6.71 (br s, 2 H). Anal. Calcd for $C_{16}H_{13}F_2N_3O_3S$: C, 52.60; H, 3.59; N, 11.50. Found: C, 52.48; H, 3.63; N, 11.28.

Step 4. Preparation of 4-[3-(difluoromethyl)-5-(4-hydroxy-3-iodophenyl)-1H-pyrazol-1-yl]benzenesulfonamide.

A solution of the compound from Step 3 (5.00 g, 14.0 mmol), sodium iodide (2.10 g, 14.0 mmol), 2.5 N sodium hydroxide (5.6 mL, 14.0 mmol) and methanol (120 mL) was cooled to 0° C. and treated dropwise with 5% aqueous sodium hypochlorite (commercial bleach) (20.84 g, 14.0 mmol). The solution was warmed to room temperature and stirred for 3 hours. The pH was adjusted to 7 by the addition of 1 N HCl, and diluted 2.5. with water until the solution became cloudy. Crystals formed that were isolated by filtration, air dried, then crystallized from hexanes/acetone to afford the title compound as a white solid (5.00 g, 72%): mp 261.8–266.4° C. $^1$H NMR (Acetone-$d_6$) 9.60 (br s 1 H), 7.96 (d, 2 H, J=8.7 Hz), 7.79 (d, 1 H, J=2.1 Hz), 7.56 (d, 2 H, J=8.7 Hz), 7.10 (dd, 1 H, J=8.4, 2.1 Hz), 6.94 (t, 1 H, J=54.4 Hz), 6.93 (d, 1 H, J=8.4 Hz), 6.84 (s, 1 H), 6.72 (br s, 2 H). FABLRMS m/z 497 (M+H).

Step 5. Preparation of 4-[3-(difluoromethyl)-5-(3-iodo-4-methoxyphenyl)-1H-pyrazol-1-yl]benzenesulfonamide.

A solution of the compound from Step 4 (2.25 g, 4.6 mmol) and potassium carbonate (1.91 g, 13.8 mmol) in acetone (40 mL) was treated with methyl iodide (710 mg, 5.0 mmol) at room temperature for 72 hours. The solution was diluted with 150 mL of ethyl acetate and washed with 1 N HCl, brine, dried over anhyd. $NiSO_4$, filtered and concentrated in vacuo. The residue was purified by flash chromatography over silica gel (eluting with hexanes:ethyl acetate 2:1) to afford the title compound as a white solid (750 mg, 32%): mp 184.2–188.4° C. $^1$H NMR (Acetone-$d_6$) 7.96 (d, 2 H, J=8.7 Hz), 7.84 (d, 1 H, J=2.4 Hz), 7.56 (d, 2 H, J=8.7 Hz), 7.28 (dd, 1 H, J=8.4, 2.4 Hz), 7.00 (d, 1 H, J=8.4 Hz), 6.94 (t, 1 H, J=54.6 Hz), 6.88 (s, 1 H), 6.73 (br s, 2 H), 3.92 (s, 3 H). Anal. Calcd for $C_{17}H_{14}F_2IN_3O_3S$: C, 40.41; H, 2.79; N, 8.32. Found: C, 40.54; H, 2.77; N, 8.31.

EXAMPLE 7

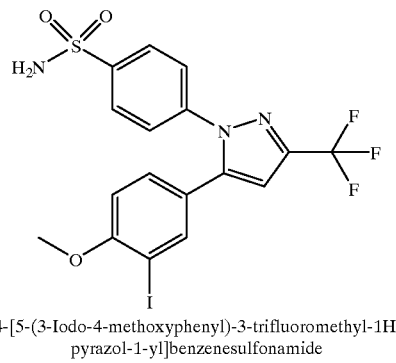

4-[5-(3-Iodo-4-methoxyphenyl)-3-trifluoromethyl-1H-pyrazol-1-yl]benzenesulfonamide Step 1. Preparation of 1-(4-benzyloxyphenyl)-4,4,4-trifluoro-1,3-butanedione.

A solution of 4-benzyloxyacetophenone (6.50 g, 29 mmol) in ether (70 mL) was cooled to 0° C. and treated with ethyl trifluoroacetate (4.12 g, 29 mmol) and 25% sodium methoxide in methanol (6.39 g, 30 mmol). The reaction was warmed to room temperature and stirred for 64.4 hours. The reaction was quenched with 3 N HCl (15 mL), extracted with ethyl acetate, washed with brine, dried over anhyd. $MgSO_4$, filtered and concentrated in vacuo to give the title compound as a yellow solid (8.91 g, 96%): mp 92.4–96.5° C. $^1$H NMR ($CDCl_3$) 15.30 (br s, 1 H), 8.86 (d, 2 H, J=8.9 Hz), 7.43 (m, 5 H), 7.08 (d, 2 H, J=8.9 Hz), 6.50 (s, 1 H) 5.16 (s, 2 H).

Step 2. Preparation of 4-[5-(4-benzyloxyphenyl)-3-(trifluoromethyl)-1H-pyrazol-1-yl]benzenesulfonamide The diketone from Step 1 (8.91 g, 28 mmol), 4-sulfonamidophenylhydrazine hydrochloride (6.77 g, 30 mmol) and ethanol (100 mL) were combined and heated to reflux for 4.4 hours. The ethanol was removed in vacuo. The residue was dissolved in ethyl acetate, washed with water, saturated NaHCO$_3$, brine, dried over anhyd. MgSO$_4$ and concentrated in vacuo to provide a brown oil. The oil was purified by flash chromatography over silica gel (eluting with 60% ethyl acetate/hexanes) to afford the title pyrazole as a white solid (8.45 g, 65%): mp 141.5–145.1° C. $^1$H NMR (CDCl$_3$) 7.89 (d, 2 H, J=8.9 Hz), 7.49 (d, 2 H, J=8.9 Hz), 7.42 (m, 5 H), 7.13 (d, 2 H, J=8.9 Hz), 6.97 (d, 2 H, J=8.9 Hz), 6.71 (s, 1 H), 5.07 (s, 2 H), 4.97 (br s, 2 H). FABLRMS m/z 474 (M+H).

Step 3. Preparation of 5-(4-hydroxyphenyl)-3-(trifluoromethyl)-1H-pyrazol-1-yl]benzenesulfonamide.

A solution of the pyrazole from Step 2 (6.30 g, 13 mmol) in dichloromethane (100 mL) was cooled to −78° C. and treated with a solution of boron trichloride (25 mmol) in dichloromethane. The reaction was stirred for 30 minutes then quenched with methanol (30 mL). The reaction mixture was concentrated in vacuo, triturated with dichloromethane and filtered to afford the title compound as a tan solid (3.55 g (70%): mp 220.3–223.8° C. $^1$H NMR (Acetone-d$_6$) 8.86 (s, 1 H), 7.95 (d, 2 H, J=8.5 Hz), 7.58 (d, 2 H, a =8.5 Hz), 7.18 (d, 2 H, J=8.5 Hz), 6.92 (s, 1 H), 6.89 (d, 2 H, J=8.6 Hz), 6.74 (br s, 2 H). FABLRMS m/z 384 (M+H).

Step 4. Preparation of 5-(4-hydroxy-3-iodophenyl)-3-(trifluoromethyl)-1H-pyrazol-1-yl]benzenesulfonamide.

A solution of the pyrazole from Step 3 (3.52 g, 9.2 mmol), NaOH (9.4 mmol), and sodium iodide (1.43 g, 9.5 mmol) in methanol (75 mL) was treated with sodium hypochlorite (9.2 mmol) at 0° C. The reaction was warmed to room temperature and stirred for 16.8 hours, then additional sodium hypochlorite (5.6 mmol) was added. The reaction was stirred an additional 4.5 hours, treated with 10% NaHSO$_3$ (30 mL), acidified with 3 N HCl, and filtered to give a white solid that was recrystallized from ethanol/water to afford the title compound as a white solid (3.57 g, 76%): mp 230.5–232.5° C. $^1$H NMR (Acetone-d$_6$) 9.93 (br s, 1 H), 7.96 (d, 2 H, J=8.7 Hz), 7.81 (d, 1 H, J=2.0 Hz), 7.60 (d, 2 H, J=8.7 Hz), 7.09 (dd, 1 H, J=8.5, 2.0 Hz), 7.00 (s, 1 H), 6.95 (d, 1 H, J=8.5 Hz), 6.79 (br s, 2 H). FABLRMS m/z 510 (M+H).

Step 5. Preparation of 4-[5-(3-iodo-4-methoxyphenyl)-3-trifluoromethyl-1H-pyrazol-1-yl]benzensulfonamide.

A solution of the compound from Step 4 (1.38 g, 2.7 mmol) and potassium carbonate (1.11 g, 8.0 mmol) in acetone (30 mL) was treated with methyl iodide (0.51 g, 3.6 mmol). The reaction was stirred at room temperature for 24 hours. The reaction was acidified with 1 N HCl (20 mL), extracted with ethyl acetate, washed with brine, dried over anhyd. MgSO$_4$, filtered, and concentrated in vacuo. The residue was crystallized from ethyl acetate/hexanes to afford the title compound as a white solid (0.21 g, 15%). The filtrate was concentrated in vacuo and the residue purified by flash chromatography over silica gel (eluting with 20% ethyl acetate/hexanes) to yield additional product (0.41 g, 29%): mp 183.1–185.6° C. $^1$H NMR (Acetone-d$_6$) 7.97 (d, 2 H, J=8.9 Hz), 7.87 (d, 1 H, J=2.2 Hz), 7.62 (d, 2 H, J=8.7 Hz), 7.28 (dd, 1 H, J=8.5, 2.2 Hz), 7.04 (s, 1 H), 7.02 (d, 1 H, J=8.5 Hz), 6.75 (brs, 2 H), 3.9 2 (s, 3 H). Anal. Calcd for C$_{17}$H$_{13}$F$_3$IN$_3$O$_3$S: C, 39.02; H, 2.50; N, 8.03. Found: C, 39.12; H. 2.49; N, 8.02.

BIOLOGICAL EVALUATION

A mammal can be injected with an appropriate amount of Example 1 and images with a PET scanner (Super PET II B) can be made at appropriate times [D. Hwang et al., J. Nuc. Med., 32, 1730–37, (1991)]. Images can be taken at the level of the organ or body portion suspected of having the COX-2 associated disorder. Also see L. Brudin et al. [Eur. J. Nuc. Med., 21, 297–305 (1994)].

From the foregoing detailed description, one skilled in the art can easily ascertain the essential characteristics of this invention, and without departing from the spirit and scope thereof, can make various changes and modifications of the invention to adapt it to various usages and conditions.

What is claimed is:

1. A method of detecting a concentration of cyclooxygenase-2 in a mammal, the method comprising:
   a) administering to the mammal a diagnostically effective amount of a cyclooxygenase-2 selective agent, which is capable of being detected in vivo; and
   b) detecting the agent so the concentration of cyclooxygenase-2 is detected.

2. The method of claim 1 wherein the agent is prepared by labeling a cyclooxygenase-2 selective compound with an isotope capable of being detected in vivo.

3. The method of claim 2 wherein the compound has the formula

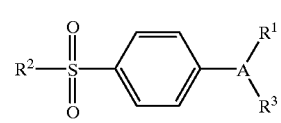

(I)

wherein A is a 5- or 6-member ring substituent selected from partially unsaturated or unsaturated heterocyclo and carbocyclic rings;

wherein R$^1$ is at least one substituent selected from heteroaryl, cycloalkyl, cycloalkenyl and aryl, wherein R$^1$ is substituted at a substitutable position with one or more radicals containing or convertible to an imaging label;

wherein R$^2$ is selected from alkyl, and amino; and wherein R$^3$ is one or more radicals selected from halo, alkyl, alkenyl, alkynyl, oxo, cyano, carboxyl, cyanoalkyl, heterocyclooxy, alkyloxy, alkylthio, alkylcarbonyl, cycloalkyl, aryl, haloalkyl, heterocyclo, cycloalkenyl, aralkyl, heterocycloalkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkylthioalkyl, aralkoxyalkyl, alkoxyaralkoxyalkyl, alkoxycarbonylalkyl, aminocarbonyl, aminocarbonylalkyl, alkylaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, N-alkyl-N-arylaminosulfonyl; or a pharmaceutically-acceptable salt thereof.

4. The method of claim 3 wherein A is a radical selected from thienyl, oxazolyl, furyl, pyrrolyl, thiazolyl, imidazolyl, benzofuryl, indenyl, benzothienyl, isoxazolyl, pyrazolyl, cyclopentenyl, cyclopentadienyl, benzindazolyl, benzopyranopyrazolyl, phenyl, and pyridyl; wherein $R^1$ is selected from 5- and 6-membered heteroaryl, and aryl selected from phenyl, biphenyl and naphhthyl, wherein $R^1$ is substituted at a substitutable position with one or more radicals selected from hydroxy, alkoxy, nitro, triflate, halo, and formyl; wherein $R^2$ is methyl or amino; and wherein $R^3$ is a radical selected from hydrido, oxo, cyano, carboxyl, lower alkoxycarbonyl, lower carboxyalkyl, lower cyanoalkyl, halo, lower alkyl, lower alkyloxy, lower cycloalkyl, phenyl, lower haloalkyl, 5- or 6-membered heterocyclo, lower hydroxyalkyl, lower aralkyl, acyl, phenylcarbonyl, lower alkoxyalkyl, 5- or 6-membered heteroaryloxv, aminocarbonyl, lower alkylaminocarbonyl, lower alkylamino, lower aminoalkyl, lower alkylaminoalkyl, phenyloxy, and lower aralkoxy; or a pharmaceutically-acceptable salt or prodrug thereof.

5. The method of claim 4 wherein A is selected from furyl, oxazolyl, isoxazolyl, imidazolyl, and pyrazolyl; wherein $R^1$ is phenyl substituted at a substitutable position with one or more radicals selected from hydroxy, nitro, triflate, halo, and formyl; wherein $R^2$ is methyl or amino; and wherein $R^3$ is a radical selected from hydrido, oxo, cyano, carboxyl, methoxycarbonyl, ethoxycarbonyl, carboxypropyl, carboxymethyl, carboxyethyl, cyanomethyl, fluoro, chloro, bromo, methyl, ethyl, isopropyl, butyl, tert-butyl, isobutyl, pentyl, hexyl, fluorometnyl, difluoromethyl, trifluoromethyl, chloromethyl, dichloromethyl, trichloromethyl, pentafluoroethyl heptafluoropropyl, fluoromethyl, difluoroethy, difluoropropyl, dichloroethyl, dichloropropyl, methoxy, ethoxy, propoxy, n-butoxy, pentoxy, cyclohexyl, phenyl, pyridyl, thienyl, thiazolyl, oxazolyl, furyl, pyrazinyl, hydroxylmethyl, hydroxylpropyl, benzyl, formyl, phenylcarbonyl, methoxymethyl, furylmethyloxy, aminocarbonyl, N-methylaminocarbonyl, N,N-dimethylaminocarbonyl, N,N-dimethylamino, N-ethylamino, N,N-dipropylamino, N-butylamino, N-methyl-N-ethylamino, aminomethyl, N,N-dimethylaminomethyl, N-methyl-N-ethylaminomethyl, benzyloxy, and phenyloxy; or a pharmaceutically-acceptable salt or prodrug thereof.

6. The method of claim 5 wherein the compound of Formula I is selected from compounds, and pharmaceutically acceptable salts and prodrug thereof, of the group consisting of 4-[3-(hydroxymethyl)-5-(4-nitrophenyl)-1H-pyrazol-1-yl]benzenesulfonamide;

4-[3-(difluoromethyl)-5-(4-hydroxyphenyl)-1H-pyrazol-1-yl]benzenesulfonamide;

4-[5-(4-hydroxyphenyl)-3-trifluoromethyl-1H-pyrazol-1-yl]benzenesulfonamide;

4-[3-(hydroxymethyl)-5-(4-hydroxyphenyl)-1H-pyrazol-1-yl]benzenesulfonamide;

4-hydroxy-5-[1-[4-(methylsulfonyl)phenyl]-4-trifluoromethyl-1H-imidazol-2-yl]pyridine;

4-[2-(4-hydroxypyridin-3-yl)-4-(trifluoromethyl)-1H-imidazol-1-yl]benzenesulfonamide;

4-[5-methyl-3-(4-hydroxyphenyl)isoxazol-4-yl]benzenesulfonamide;

4-[5-hydroxymethyl-3-(4-hydroxyphenyl)isoxazol-4-yl]benzenesulfonamide;

4-[2-methyl-4-(4-hydroxyphenyl)-5-oxazolyl]benzenesulfonamide;

4-[5-(4-hydroxyphenyl)-2-(trifluoromethyl)-4-oxazolyl]benzenesulfonamide;

4-[3-(difluoromethyl)-5-(3-iodo-4-hydroxyphenyl)-1H-pyrazol-1-yl]benzenesulfonamide;

4-[5-(3-iodo-4-hydroxyphenyl)-3-trifluoromethyl-1H-pyrazol-1-yl]benzenesulfonamide;

4-[3-(hydroxymethyl)-5-(3-iodo-4-hydroxyphenyl)-1H-pyrazol-1-yl]benzenesulfonamide;

4-[3-(difluoromethyl)-5-(4-nitrophenyl) -1H-pyrazol-1-yl]benzenesulfonamide;

4-[5-(4-nitrophenyl)-3-(trifluoromethyl)-1H-pyrazol-1-yl]benzenesulfonamide;

4-[3-(difluoromethyl)-5-(4-nitrophenyl)-1H-pyrazol-1-yl]benzenesulfonamide;

4-nitro-5-[1-[4-(methylsulfonyl)phenyl]-4-trifluoromethyl-1H-imidazol-2-yl]pyridine;

4-[2-(4-nitropyridin-3-yl)-4-(trifluoromethyl)-1H-imidazol-1-yl]benzenesulfonamide;

4-[5-methyl-3-(4-nitrophenyl)isoxazol-4-yl]benzenesulfonamide;

4-[5-hydroxymethyl-3-(4-nitrophenyl)isoxazol-4-yl]benzenesulfonamide;

4-[2-methyl-4-(4-nitrophenyl)-5-oxazolyl]benzenesulfonamide; and

4-[5-(4-nitrophenyl)-2-(trifluoromethyl)-4-oxazolyl]benzenesulfonamide.

7. The method of claim 2, wherein the isotope is capable of being detected by PET.

8. The method of claim 7, wherein the compound is labeled with one or more isotopes selected from 11C, $^{123}$I, $^{73}$Se, $^{76}$Br, $^{77}$Br, and $^{18}$F.

9. The method of claim 7, wherein the compound is labeled with $^{11}$C or $^{18}$F.

10. The method of claim 1 wherein the detected cyclooxygenase-2 is associated with a condition selected from inflammation, arthritis, neoplasia and central nervous system disorders.

11. The method of claim 1 wherein the agent is selected from compounds, and pharmaceutically acceptable salts thereof, of the group consisting of 4-[3-(hydroxymethyl)-5-[4-($^{18}$F) fluorophenyl]-1H-pyrazol-1-yl]benzenesulfonamide;

4-[3-(difluoromethyl)-5-[4-($^{11}$C)methoxyphenyl]-1H-pyrazol-1-yl]benzenesulfonamide;

4-[5-[4-($^{11}$C)methoxyphenyl]-3-trifluoromethyl-1H-pyrazol-1-yl]benzenesulfonamide;

4-[3-(hydroxymethyl)-5-[4-($^{11}$C)methoxyphenyl]-1H-pyrazol-1-yl]benzenesulfonamide;

4-($^{11}$C)methoxy-5-[1-[4-(methylsulfonyl)phenyl]-4-trifluoromethyl-1H-imidazol-2-yl]pyridine;

4-[2-[4-($^{11}$C)methoxypyridin-3-yl]-4-(trifluoromethyl)-1H-imidazol-1-yl]benzenesulfonamide;

4-[5-methyl-3-[4-($^{11}$C)methoxyphenyl]isoxazol-4-yl]benzenesulfonamide;

4-[5-hydroxymethyl-3-[4-($^{11}$C)methoxyphenyl]isoxazol-4-yl]benzenesulfonamide;

4-[2-methyl-4-[4-($^{11}$C)methoxyphenyl]-5-oxazolyl]benzenesulfonamide;

4-[5-[4-($^{11}$C)methoxyphenyl]-2-(trifluoromethyl)-4-oxazolyl]benzenesulfonamide;

4-[3-(difluoromethyl)-5-[3-($^{125}$I)iodo-4-($^{11}$C)methoxyphenyl]-1H-pyrazol-1-yl]benzenesulfonamide;

4-[5-[3-($^{125}$I)iodo-4-($^{11}$C)methoxyphenyl]-3-trifluoromethyl-1H-pyrazol-1-yl]benzenesulfonamide;

4-[3-(hydroxymethyl)-5-[3-($^{125}$I) iodo-4-($^{11}$C)methoxyphenyl]-1H-pyrazol-1-yl]benzenesulfonamide;

4-[3-(difluoromethyl)-5-[4-($^{18}$F) fluorophenyl]-1H-pyrazol-1-yl]benzenesulfonamide;

4-[5-[4-($^{18}$F) fluorophenyl]-3-(trifluoromethyl) -1H-pyrazol-1-yl]benzenesulfonamide;

4-[3-(difluoromethyl)-5-[4-($^{18}$F) fluorophenyl]-1H-pyrazol-1-yl]benzenesulfonamide;

4-($^{18}$F)fluoro-5-[1-[4-(methylsulfonyl)phenyl]-4-trifluoromethyl-1H-imidazol-2-yl]pyridine;

4-[2-(4-($^{18}$F) fluoropyridin-3-yl) -4-(trifluoromethyl) -1H-imidazol-1-yl]benzenesulfonamide;

4-[5-methyl-3-[4-($^{18}$F) fluorophenyl]isoxazol-4-yl] benzenesulfonamide;

4-[5-hydroxymethyl-3-[4-($^{18}$F) fluorophenyl]isoxazol-4-yl]benzenesulfonamide;

4-[2-methyl-4-[4-($^{18}$F)fluorophenyl]-5-oxazolyl] benzenesulfonamide; and

4-[5-[4-($^{18}$F)fluorophenyl]-2-(trifluoromethyl)-4-oxazolyl]benzenesulfonamide.

12. A method of localizing and quantifying cyclooxygenase-2 in a mammal, said method comprising a) preparing a labeled compound, which selectively binds to cyclooxygenase-2 and which contains an isotope capable of emitting radiation;

b) administering to said mammal a diagnostically effective amount of the labeled compound; and c) detecting an emission from the compound administered to the mammal so that the cyclooxygenase-2 in the mammal is localized.

13. The method of claim 12 wherein the emission is detected by an technique selected from SPECT and PET.

14. The method of claim 13 wherein the emission is detected by PET.

15. The method of claim 12 wherein the isotope is capable of emitting gamma or positron radiation.

16. The method of claim 15 wherein the isotope is selected from isotopes of carbon, oxygen, nitrogen, selenium, bromine, iodine and fluorine.

17. The method of claim 16, wherein the compound is labeled with one or more isotopes selected from $^{11}$C, $^{123}$I, $^{73}$Se, $^{76}$Br, $^{77}$Br, and $^{18}$F.

18. The method of claim 17 wherein the isotope is $^{18}$F or $^{11}$C.

19. A method of detecting neoplasia in a mammal, said method comprising a) preparing a compound which selectively binds to cyclooxygenase-2 and which is labeled with an isotope capable of emitting gamma or positron radiation b) administering to said mammal a diagnostically effective amount of the labeled compound; and c) detecting an emission from the compound administered to the mammal so that the neoplasia in the mammal is localized.

20. The method of claim 19, wherein the compound is labeled with, one or more isotopes selected from $^{11}$C, $^{123}$I, $^{73}$Se, $^{76}$Br, $^{77}$Br, and $^{18}$F.

21. A method of localizing and quantifying cyclooxygenase-2 in a mammal, the method comprising:

a) preparing a compound which selectively binds to cyclooxygenase-2 and which is labeled with an isotope capable of emitting gamma radiation;

b) administering to said mammal a diagnostically effective amount of the labeled compound; and c) detecting the gamma emission from the compound administered to the mammal so that the cyclooxygenase-2 in the mammal is localized.

22. The method of claim 21, wherein the isotope is $^{125}$I.

23. The method of claim 22, wherein the cyclooxygenase-2 concentration is associated with a condition selected from inflammation, arthritis, neoplasia and central nervous system disorders.

* * * * *